(12) United States Patent
Fujii

(10) Patent No.: US 7,435,546 B2
(45) Date of Patent: Oct. 14, 2008

(54) SYSTEM TO DETECT INDUCIBLE TRANSLOCATION

(75) Inventor: Hodaka Fujii, New York, NY (US)

(73) Assignee: New York University, New York, NY (US)

( * ) Notice: Subject to any disclaimer, the term of this patent is extended or adjusted under 35 U.S.C. 154(b) by 259 days.

(21) Appl. No.: 11/170,751

(22) Filed: Jun. 29, 2005

(65) Prior Publication Data

US 2006/0014188 A1  Jan. 19, 2006

Related U.S. Application Data

(60) Provisional application No. 60/584,069, filed on Jun. 30, 2004.

(51) Int. Cl.
*C12Q 1/68* (2006.01)
*C12Q 1/66* (2006.01)
*C12N 15/63* (2006.01)

(52) U.S. Cl. .............................................. 435/6; 435/8

(58) Field of Classification Search ....................... None
See application file for complete search history.

(56) References Cited

OTHER PUBLICATIONS

No references.*

* cited by examiner

*Primary Examiner*—David Guzo
*Assistant Examiner*—Michele K. Joike
(74) *Attorney, Agent, or Firm*—Klauber & Jackson L.L.C.

(57) ABSTRACT

The present invention relates to a novel method for screening to identify/detect polypeptides capable of translocating into or out of the nucleus of a cell in response to induction by an external stimulus or stimuli. Kits for practicing the method of the invention are also encompassed by the present invention.

28 Claims, 4 Drawing Sheets

Fig. 1A pLGV vector

Fig. 1B LexA-hCD2 reporter

Fig. 1C Ligand stimulation (-)    Ligand stimulation (+)

Fig. 2A
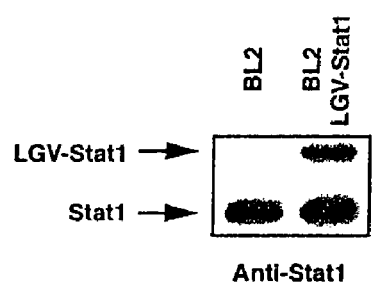
Fig. 2B
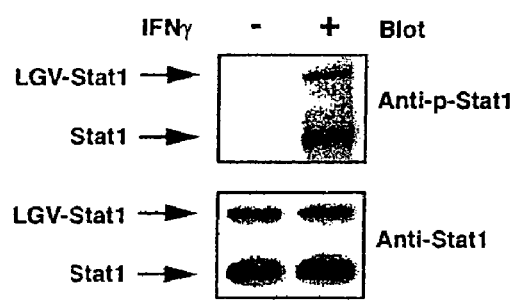
Fig. 2C
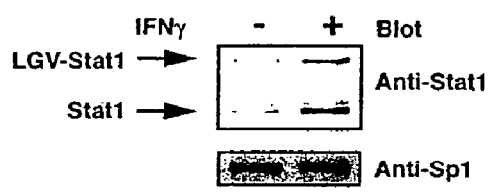
Fig. 2D
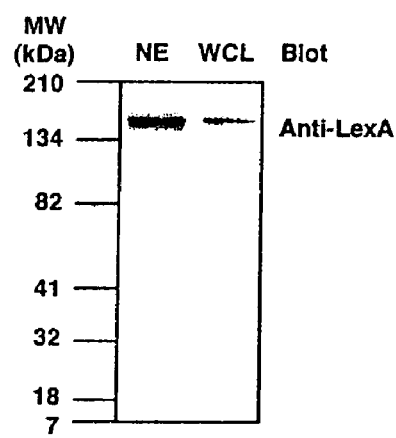
Fig. 2E
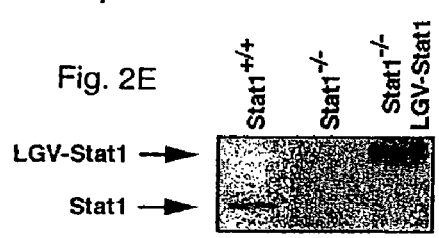
Fig. 2F
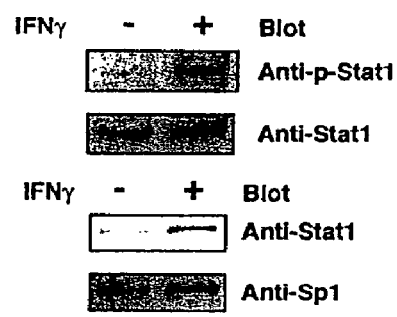
Fig. 2G Fig. 3A
pLG vector
Fig. 3B
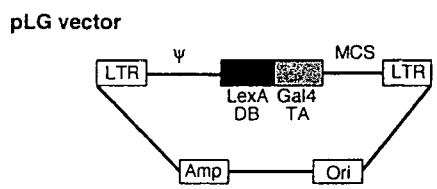
LexA-d1EGFP reporter
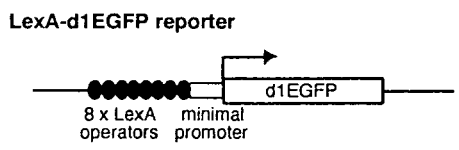
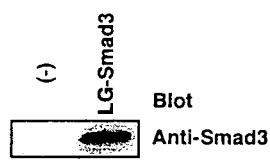
Fig. 3C
Fig. 3D
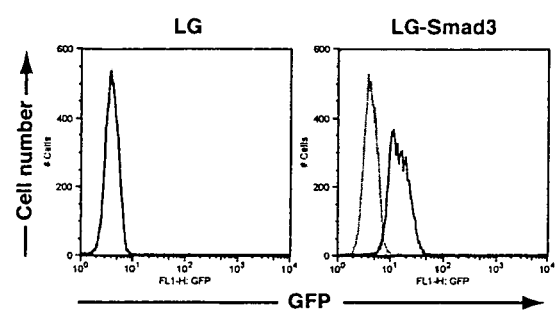
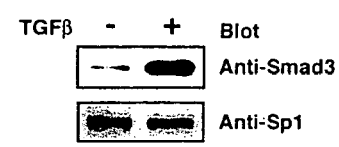
Fig. 3E
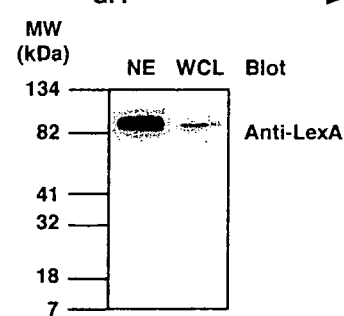
Fig. 3F Fig. 4A
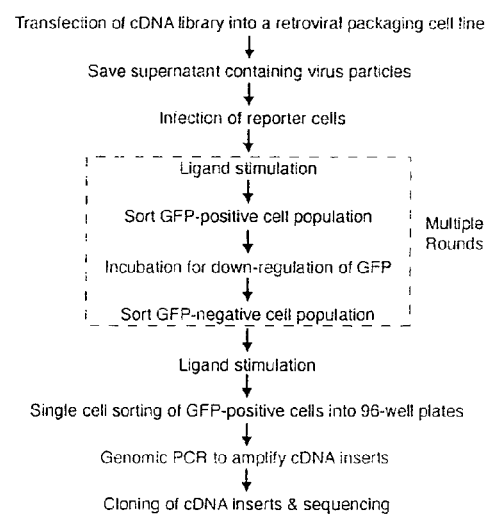
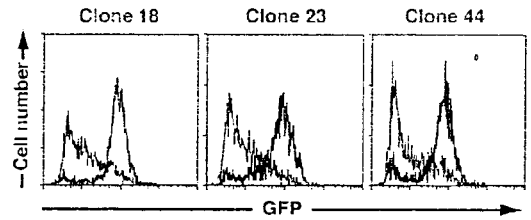
Fig. 4F
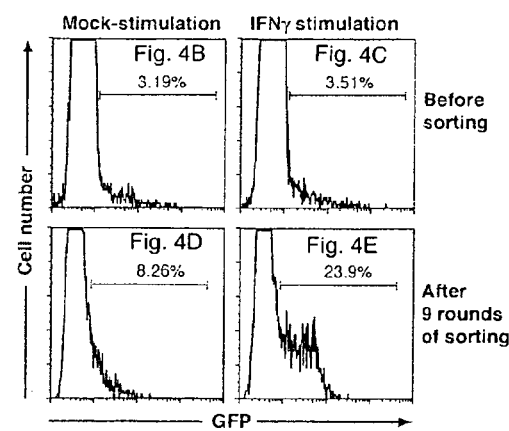
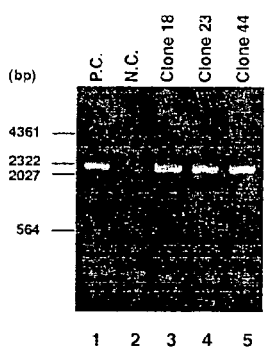
Fig. 4G

SEQUENCE LISTING

<160> NUMBER OF SEQ ID NOS: 6

<210> SEQ ID NO 1
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1
caatggatga tgtatataac tatctattcg at                             32

<210> SEQ ID NO 2
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 2
tccccccttt ttctggagac taaataaaat                                30

<210> SEQ ID NO 3
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 3
acaggatcca tgtcacagtg gttcgagctt cag                            33

```
<210> SEQ ID NO 4
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 4
cgggtcgacg tgtttatact gtgctcatca tactgtc                        37

<210> SEQ ID NO 5
<211> LENGTH: 5597
<212> TYPE: DNA
<213> ORGANISM: Artificial Sequence
<220> FEATURE:
<223> OTHER INFORMATION: synthetic plasmid construct

<400> SEQUENCE: 5
cccgggaggt accgagctct tacgcgtgct agctcgagat ctaagtaagc ttggcattcc    60
ggtactgttg gtaaaatgga agacgccaaa aacataaaga aaggcccggc gccattctat   120
cctctagagg atggaaccgc tggagagcaa ctgcataagg ctatgaagag atacgccctg   180
gttcctggaa caattgcttt tacagatgca catatcgagg tgaacatcac gtacgcggaa   240
tacttcgaaa tgtccgttcg gttggcagaa gctatgaaac gatatgggct gaatacaaat   300
cacagaatcg tcgtatgcag tgaaaactct cttcaattct ttatgccggt gttgggcgcg   360
ttatttatcg gagttgcagt tgcgcccgcg aacgacattt ataatgaacg tgaattgctc   420
aacagtatga acatttcgca gcctaccgta gtgtttgttt ccaaaaaggg gttgcaaaaa   480
attttgaacg tgcaaaaaaa attaccaata atccagaaaa ttattatcat ggattctaaa   540
acggattacc agggatttca gtcgatgtac acgttcgtca catctcatct acctcccggt   600
tttaatgaat acgattttgt accagagtcc tttgatcgtg acaaaacaat tgcactgata   660
atgaattcct ctggatctac tgggttacct aagggtgtgg cccttccgca tagaactgcc   720
tgcgtcagat tctcgcatgc cagagatcct atttttggca atcaaatcat tccggatact   780
gcgattttaa gtgttgttcc attccatcac ggttttggaa tgtttactac actcggatat   840
ttgatatgtg gatttcgagt cgtcttaatg tatagatttg aagaagagct gttttttacga   900 tcccttcagg attacaaaat tcaaagtgcg ttgctagtac caaccctatt ttcattcttc   960
gccaaaagca ctctgattga caaatacgat ttatctaatt tacacgaaat tgcttctggg  1020
ggcgcacctc tttcgaaaga agtcggggaa gcggttgcaa acgcttcca tcttccaggg  1080 atacgacaag gatatgggct cactgagact acatcagcta ttctgattac acccgagggg  1140
gatgataaac cgggcgcggt cggtaaagtt gttccatttt ttgaagcgaa ggttgtggat  1200
ctggataccg ggaaaacgct gggcgttaat cagagaggcg aattatgtgt cagaggacct  1260
atgattatgt ccggttatgt aaacaatccg gaagcgacca acgccttgat tgacaaggat  1320
ggatggctac attctggaga catagcttac tgggacgaag acgaacactt cttcatagtt  1380
gaccgcttga agtcttttaat taaatacaaa ggatatcagg tggcccccgc tgaattggaa  1440
tcgatattgt tacaacaccc caacatcttc gacgcgggcg tggcaggtct tcccgacgat  1500
gacgccggtg aacttcccgc cgccgttgtt gttttggagc acgaaagac gatgacgaa  1560 aaagagatcg tggattacgt cgccagtcaa gtaacaaccg cgaaaaagtt gcgcggagga  1620
gttgtgtttg tggacgaagt accgaaaggt cttaccggaa aactcgacgc aagaaaaatc  1680
```

-continued

```
agagagatcc tcataaaggc caagaagggc ggaaagtcca aattgtaaaa tgtaactgta   1740
ttcagcgatg acgaaattct tagctattgt aatactgcga tgagtggcag ggcggggcgt   1800
aattttttta aggcagttat tggtgccctt aaacgcctgg tgctacgcct gaataagtga   1860
taataagcgg atgaatggca gaaattcgcc ggatctttgt gaaggaacct tacttctgtg   1920
gtgtgacata attggacaaa ctacctacag agatttaaag ctctaaggta aatataaaat   1980
ttttaagtgt ataatgtgtt aaactactga ttctaattgt ttgtgtattt tagattccaa   2040
cctatggaac tgatgaatgg gagcagtggt ggaatgcctt aatgaggaa aacctgtttt    2100 gctcagaaga aatgccatct agtgatgatg aggctactgc tgactctcaa cattctactc   2160
ctccaaaaaa gaagagaaag gtagaagacc ccaaggactt ccttcagaa ttgctaagtt    2220 ttttgagtca tgctgtgttt agtaatagaa ctcttgcttg ctttgctatt tacaccacaa   2280
aggaaaaagc tgcactgcta tacaagaaaa ttatggaaaa atattctgta acctttataa   2340
gtaggcataa cagttataat cataacatac tgttttttct tactccacac aggcatagag   2400
tgtctgctat taataactat gctcaaaaat tgtgtaccttt agcttttta atttgtaaag   2460 gggttaataa ggaatatttg atgtatagtg ccttgactag agatcataat cagccatacc   2520
acatttgtag aggttttact tgctttaaaa aacctcccac acctcccct gaacctgaaa    2580 cataaaatga atgcaattgt tgttgttaac ttgtttattg cagcttataa tggttacaaa   2640
taaagcaata gcatcacaaa tttcacaaat aaagcatttt tttcactgca ttctagttgt   2700
ggtttgtcca aactcatcaa tgtatcttat catgtctgga tccgtcgacc gatgcccttg   2760
agagccttca acccagtcag ctccttccgg tgggcgcggg gcatgactat cgtcgccgca   2820
cttatgactg tcttctttat catgcaactc gtaggacagg tgccggcagc gctcttccgc   2880
ttcctcgctc actgactcgc tgcgctcggt cgttcggctg cggcgagcgg tatcagctca   2940
ctcaaaggcg gtaatacggt tatccacaga atcaggggat aacgcaggaa agaacatgtg   3000
agcaaaaggc cagcaaaagg ccaggaaccg taaaaaggcc gcgttgctgg cgttttttcca  3060 taggctccgc cccctgacg agcatcacaa aaatcgacgc tcaagtcaga ggtggcgaaa    3120
cccgacagga ctataaagat accaggcgtt tccccctgga agctccctcg tgcgctctcc   3180
tgttccgacc ctgccgctta ccggatacct gtccgccttt ctcccttcgg gaagcgtggc   3240
gctttctcaa tgctcacgct gtaggtatct cagttcggtg taggtcgttc gctccaagct   3300
gggctgtgtg cacgaacccc ccgttcagcc cgaccgctgc gccttatccg gtaactatcg   3360
tcttgagtcc aacccggtaa gacacgactt atcgccactg gcagcagcca ctggtaacag   3420
gattagcaga gcgaggtatg taggcggtgc tacagagttc ttgaagtggt ggcctaacta   3480
cggctacact agaaggacag tatttggtat ctgcgctctg ctgaagccag ttaccttcgg   3540
aaaaagagtt ggtagctctt gatccggcaa acaaaccacc gctggtagcg tggtttttt    3600 tgtttgcaag cagcagatta cgcgcagaaa aaaaggatct caagaagatc ctttgatctt   3660
ttctacgggg tctgacgctc agtggaacga aaactcacgt taagggattt tggtcatgag   3720
attatcaaaa aggatcttca cctagatcct ttaaattaa aatgaagtt ttaaatcaat     3780 ctaaagtata tatgagtaaa cttggtctga cagttaccaa tgcttaatca gtgaggcacc   3840
tatctcagcg atctgtctat ttcgttcatc catagttgcc tgactccccg tcgtgtagat   3900
aactacgata cgggagggct taccatctgg ccccagtgct gcaatgatac cgcgagaccc   3960
acgctcaccg gctccagatt tatcagcaat aaaccagcca gcggaaggg ccgagcgcag    4020 aagtggtcct gcaactttat ccgcctccat ccagtctatt aattgttgcc gggaagctag   4080
```

```
agtaagtagt tcgccagtta atagtttgcg caacgttgtt gccattgcta caggcatcgt    4140
ggtgtcacgc tcgtcgtttg gtatggcttc attcagctcc ggttcccaac gatcaaggcg    4200
agttacatga tcccccatgt tgtgcaaaaa agcggttagc tccttcggtc ctccgatcgt    4260
tgtcagaagt aagttggccg cagtgttatc actcatggtt atggcagcac tgcataattc    4320
tcttactgtc atgccatccg taagatgctt ttctgtgact ggtgagtact caaccaagtc    4380
attctgagaa tagtgtatgc ggcgaccgag ttgctcttgc ccggcgtcaa tacgggataa    4440
taccgcgcca catagcagaa ctttaaaagt gctcatcatt ggaaaacgtt cttcggggcg    4500
aaaactctca aggatcttac cgctgttgag atccagttcg atgtaaccca ctcgtgcacc    4560
caactgatct tcagcatctt ttactttcac cagcgtttct gggtgagcaa aacaggaag    4620 gcaaaatgcc gcaaaaaagg gaataagggc gacacggaaa tgttgaatac tcatactctt    4680
cctttttcaa tattattgaa gcatttatca gggttattgt ctcatgagcg gatacatatt    4740
tgaatgtatt tagaaaaata aacaaatagg ggttccgcgc acatttcccc gaaaagtgcc    4800
acctgacgcg ccctgtagcg gcgcattaag cgcggcgggt gtggtggtta cgcgcagcgt    4860
gaccgctaca cttgccagcg ccctagcgcc cgctcctttc gctttcttcc cttcctttct    4920
cgccacgttc gccggctttc cccgtcaagc tctaaatcgg gggctccctt tagggttccg    4980
atttagtgct ttacggcacc tcgaccccaa aaaacttgat tagggtgatg gttcacgtag    5040
tgggccatcg ccctgataga cggtttttcg ccctttgacg ttggagtcca cgttctttaa    5100
tagtggactc ttgttccaaa ctggaacaac actcaaccct atctcggtct attcttttga    5160
tttataaggg attttgccga tttcggccta ttggttaaaa aatgagctga tttaacaaaa    5220
atttaacgcg aattttaaca aaatattaac gtttacaatt tcccattcgc cattcaggct    5280
gcgcaactgt tgggaagggc gatcggtgcg ggcctcttcg ctattacgcc agcccaagct    5340
accatgataa gtaagtaata ttaaggtacg tggaggtttt acttgcttta aaaaacctcc    5400
cacacctccc cctgaacctg aaacataaaa tgaatgcaat tgttgttgtt aacttgttta    5460
ttgcagctta taatggttac aaataaagca atagcatcac aaatttcaca aataaagcat    5520
ttttttcact gcattctagt tgtggtttgt ccaaactcat caatgtatct tatggtactg    5580
taactgagct aacataa                                                  5597

<210> SEQ ID NO 6
<211> LENGTH: 4818
<212> TYPE: DNA
<213> ORGANISM: Artificial Sequence
<220> FEATURE:
<223> OTHER INFORMATION: synthetic plasmid construct

<400> SEQUENCE: 6
ggtaccgagc tcttacgcgt gctagcccgg gctcgagatc tgcgatctaa gtaagcttgg      60
cattccggta ctgttggtaa agccaccatg gaagacgcca aaaacataaa gaaaggcccg     120
gcgccattct atccgctgga agatggaacc gctggagagc aactgcataa ggctatgaag     180
agatacgccc tggttcctgg aacaattgct tttacagatg cacatatcga ggtggacatc     240
acttacgctg agtacttcga aatgtccgtt cggttggcag aagctatgaa acgatatggg     300
ctgaatacaa atcacagaat cgtcgtatgc agtgaaaact ctcttcaatt ctttatgccg     360
gtgttgggcg cgttatttat cggagttgca gttgcgcccg cgaacgacat ttataatgaa     420
cgtgaattgc tcaacagtat gggcatttcg cagcctaccg tggtgttcgt ttccaaaaag     480
```

```
gggttgcaaa aaattttgaa cgtgcaaaaa aagctcccaa tcatccaaaa aattattatc    540
atggattcta aaacggatta ccagggattt cagtcgatgt acacgttcgt cacatctcat    600
ctacctcccg gttttaatga atacgatttt gtgccagagt ccttcgatag ggacaagaca    660
attgcactga tcatgaactc ctctggatct actggtctgc ctaaaggtgt cgctctgcct    720
catagaactg cctgcgtgag attctcgcat gccagagatc ctattttggg caatcaaatc    780
attccggata ctgcgatttt aagtgttgtt ccattccatc acggttttgg aatgtttact    840
acactcggat atttgatatg tggatttcga gtcgtcttaa tgtatagatt tgaagaagag    900
ctgtttctga ggagccttca ggattacaag attcaaagtg cgctgctggt gccaacccta    960
ttctccttct tcgccaaaag cactctgatt gacaaatacg atttatctaa tttacacgaa   1020
attgcttctg gtggcgctcc cctctctaag gaagtcgggg aagcggttgc caagaggttc   1080
catctgccag gtatcaggca aggatatggg ctcactgaga ctacatcagc tattctgatt   1140
acacccgagg gggatgataa accgggcgcg gtcggtaaag ttgttccatt ttttgaagcg   1200
aaggttgtgg atctggatac cgggaaaacg ctgggcgtta atcaaagagg cgaactgtgt   1260
gtgagaggtc ctatgattat gtccggttat gtaaacaatc cggaagcgac caacgccttg   1320
attgacaagg atggatggct acattctgga gacatagctt actgggacga agacgaacac   1380
ttcttcatcg ttgaccgcct gaagtctctg attaagtaca aaggctatca ggtggctccc   1440
gctgaattgg aatccatctt gctccaacac cccaacatct tcgacgcagg tgtcgcaggt   1500
cttcccgacg atgacgccgg tgaacttccc gccgccgttg ttgttttgga gcacggaaag   1560
acgatgacgg aaaaagagat cgtggattac gtcgccagtc aagtaacaac cgcgaaaaag   1620
ttgcgcggag gagttgtgtt tgtggacgaa gtaccgaaag gtcttaccgg aaaactcgac   1680
gcaagaaaaa tcagagagat cctcataaag gccaagaagg gcggaaagat cgccgtgtaa   1740
ttctagagtc ggggcggccg gccgcttcga gcagacatga taagatacat tgatgagttt   1800
ggacaaacca caactagaat gcagtgaaaa aaatgcttta tttgtgaaat ttgtgatgct   1860
attgctttat ttgtaaccat tataagctgc aataaacaag ttaacaacaa caattgcatt   1920
cattttatgt ttcaggttca ggggaggtg tgggaggttt tttaaagcaa gtaaaacctc   1980
tacaaatgtg gtaaaatcga taaggatccg tcgaccgatg cccttgagag ccttcaaccc   2040
agtcagctcc ttccggtggg cgcggggcat gactatcgtc gccgcactta tgactgtctt   2100
ctttatcatg caactcgtag gacaggtgcc ggcagcgctc ttccgcttcc tcgctcactg   2160
actcgctgcg ctcggtcgtt cggctgcggc gagcggtatc agctcactca aaggcggtaa   2220
tacggttatc cacagaatca ggggataacg caggaaagaa catgtgagca aaaggccagc   2280
aaaaggccag gaaccgtaaa aaggccgcgt tgctggcgtt tttccatagg ctccgccccc   2340
ctgacgagca tcacaaaaat cgacgctcaa gtcagaggtg gcgaaacccg acaggactat   2400
aaagatacca ggcgtttccc cctggaagct ccctcgtgcg ctctcctgtt ccgaccctgc   2460
cgcttaccgg atacctgtcc gcctttctcc cttcgggaag cgtggcgctt tctcaatgct   2520
cacgctgtag gtatctcagt tcggtgtagg tcgttcgctc caagctgggc tgtgtgcacg   2580
aaccccccgt tcagcccgac cgctgcgcct tatccggtaa ctatcgtctt gagtccaacc   2640
cggtaagaca cgacttatcg ccactggcag cagccactgg taacaggatt agcagagcga   2700
ggtatgtagg cggtgctaca gagttcttga agtggtggcc taactacggc tacactagaa   2760
ggacagtatt tggtatctgc gctctgctga agccagttac cttcggaaaa agagttggta   2820
gctcttgatc cggcaaacaa accaccgctg gtagcggtgg ttttttttgtt tgcaagcagc   2880
```

```
agattacgcg cagaaaaaaa ggatctcaag aagatccttt gatcttttct acggggtctg    2940
acgctcagtg gaacgaaaac tcacgttaag ggattttggt catgagatta tcaaaaagga    3000
tcttcaccta gatccttta aattaaaaat gaagttttaa atcaatctaa agtatatatg    3060
agtaaacttg gtctgacagt taccaatgct taatcagtga ggcacctatc tcagcgatct    3120
gtctatttcg ttcatccata gttgcctgac tccccgtcgt gtagataact acgatacggg    3180
agggcttacc atctggcccc agtgctgcaa tgataccgcg agacccacgc tcaccggctc    3240
cagatttatc agcaataaac cagccagccg gaagggccga gcgcagaagt ggtcctgcaa    3300
ctttatccgc ctccatccag tctattaatt gttgccggga agctagagta agtagttcgc    3360
cagttaatag tttgcgcaac gttgttgcca ttgctacagg catcgtggtg tcacgctcgt    3420
cgtttggtat ggcttcattc agctccggtt cccaacgatc aaggcgagtt acatgatccc    3480
ccatgttgtg caaaaaagcg gttagctcct tcggtcctcc gatcgttgtc agaagtaagt    3540
tggccgcagt gttatcactc atggttatgg cagcactgca taattctctt actgtcatgc    3600
catccgtaag atgcttttct gtgactggtg agtactcaac caagtcattc tgagaatagt    3660
gtatgcggcg accgagttgc tcttgcccgg cgtcaatacg ggataatacc gcgccacata    3720
gcagaacttt aaaagtgctc atcattggaa aacgttcttc ggggcgaaaa ctctcaagga    3780
tcttaccgct gttgagatcc agttcgatgt aacccactcg tgcacccaac tgatcttcag    3840
catcttttac tttcaccagc gtttctgggt gagcaaaaac aggaaggcaa aatgccgcaa    3900
aaaagggaat aagggcgaca cggaaatgtt gaatactcat actcttcctt tttcaatatt    3960
attgaagcat ttatcagggt tattgtctca tgagcggata catatttgaa tgtatttaga    4020
aaaataaaca aataggggtt ccgcgcacat ttccccgaaa agtgccacct gacgcgccct    4080
gtagcggcgc attaagcgcg gcgggtgtgg tggttacgcg cagcgtgacc gctacacttg    4140
ccagcgccct agcgcccgct cctttcgctt tcttcccttc ctttctcgcc acgttcgccg    4200
gctttccccg tcaagctcta aatcgggggc tccctttagg gttccgattt agtgctttac    4260
ggcacctcga ccccaaaaaa cttgattagg gtgatggttc acgtagtggg ccatcgccct    4320
gatagacggt ttttcgccct ttgacgttgg agtccacgtt ctttaatagt ggactcttgt    4380
tccaaactgg aacaacactc aaccctatct cggtctattc ttttgattta agggattt    4440 tgccgatttc ggcctattgg ttaaaaaatg agctgattta acaaaaattt aacgcgaatt    4500
ttaacaaaat attaacgttt acaatttccc attcgccatt caggctgcgc aactgttggg    4560
aagggcgatc ggtgcgggcc tcttcgctat tacgccagcc caagctacca tgataagtaa    4620
gtaatattaa ggtacgggag gtacttggag cggccgcaat aaaatatctt tatttcatt    4680 acatctgtgt gttggttttt tgtgtgaatc gatagtacta acatacgctc tccatcaaaa    4740
caaaacgaaa caaaacaaac tagcaaaata ggctgtcccc agtgcaagtg caggtgccag    4800
aacatttctc tatcgata                                                  4818
```

SYSTEM TO DETECT INDUCIBLE TRANSLOCATION

CROSS REFERENCE TO RELATED APPLICATION

This application claims priority under 35 USC § 119(e) from U.S. Provisional Application Ser. No. 60/584,069, filed Jun. 30, 2004, which application is herein specifically incorporated by reference in its entirety.

FIELD OF INVENTION

The present invention relates to molecular biology, protein-protein interactions, and signal transduction pathways that initiate at the cell surface and result in nuclear translocation of downstream signaling proteins. Specifically, the present invention is directed to a novel method for identifying/detecting polypeptides capable of translocating either to or from the nucleus in response to an extracellular stimulus. The present method also serves to identify nucleic acid sequences encoding such polypeptides. Kits for practicing the present methods are also described.

BACKGROUND OF INVENTION

Several publications and patent documents are referenced in this application in order to more fully describe the state of the art to which this invention pertains. The disclosure of each of these publications and documents is incorporated by reference herein.

Extracellular signaling molecules bound to cell surface receptors can regulate nuclear function with consequences for cell proliferation, differentiation, and function. To regulate nuclear function, signals must be transduced across the nuclear envelope to propagate the signal from the cytoplasm to the nucleus. Many signaling responses induce the nuclear translocation of transcription factors, kinases and others (Cyert. (2001) J. Biol. Chem. 276, 20805-20808; Brivanlou et al. (2002) Science 295, 813-818).

Diverse mechanisms exist that regulate how these molecules are activated to move or translocate into and out of the nucleus. Phosphorylation is one of the most extensively characterized post-translational modifications that contributes to the ability of molecules to undergo nuclear translocation. In signal transduction from type I and type II cytokine receptors, for example, signal transducer and activator of transcription (Stat) proteins, which usually reside within the cytoplasm, become activated upon selective phosphorylation of tyrosine residues by Jak protein tyrosine kinases. Phosphorylated Stat proteins subsequently form complexes (e.g., homodimers), thus becoming active transcription factors that translocate into the nucleus to regulate transcription of their target genes (Ihle (1996) Cell 84, 331-334; Stark et al. (1998) Annu. Rev. Biochem. 67, 227-264; Levy et al. (2002) Nat. Rev. Mol. Cell Biol. 3, 651-662). Serine phosphorylation also plays an important role in nuclear translocation of Smad transcription factors in transforming growth factor-β (TGFβ) signaling (Massagué. (2000) Nat. Rev. Mol. Cell Biol. 1, 169-178). In addition to transcription factors, other signaling molecules, such as mitogen-activated protein kinase, also translocate into the nucleus upon targeted phosphorylation (Chen et al. (1992) Mol. Cell. Biol. 12, 915-927).

Calcium signaling, however, activates the phosphatase calcineurin, which in turn dephosphorylates and induces nuclear localization of the cytoplasmic components of nuclear factor of activated T cells (NFATc) (Crabtree et al. (2002) Cell 109, S67-S79). In contrast, lipopolysaccharide and inflammatory cytokines activate nuclear factor κB (NF-κB) transcription factor to move into the nucleus by the targeted phosphorylation and subsequent degradation of IκB (Baeuerle et al. (1996) Cell 87, 13-20; Baldwin. (1996) Annu. Rev. Immunol. 14, 649-681). Proteolytic cleavage is used differently for signal-induced nuclear translocation as revealed in activation of sterol regulatory element binding proteins (SREBP) in cholesterol metabolism (Horton et al. (2002) J. Clin. Invest. 109, 1125-1131) or in Notch signaling (Schroeter et al. (1998) Nature 393, 382-386; Struhl et al. (1998) Cell 93, 649-660). These diverse mechanisms of regulated nuclear translocation have made it difficult to devise general methods to identify proteins whose translocation into the nucleus is induced by extracellular stimuli.

As described herein below, the present invention addresses the need for an assay that can identify proteins whose translocation into the nucleus is induced by extracellular stimuli.

SUMMARY

The present inventor has developed a novel system, designated herein as the inducible translocation trap (ITT) system, for identifying proteins capable of translocating into the nucleus upon induction by extracellular stimuli. ITT uses reporter gene expression as an assay for nuclear translocation and is not reliant on the availability of information pertaining to the particular molecules in question. It is, therefore, well suited to high throughput analyses directed to screening large libraries comprising, for example, Expressed Sequence Tags (ESTs). The present inventor has shown that inducible translocation of Stat1 or Smad3 can be detected by interferon-γ (IFNγ)- or TGFβ-induced reporter gene expression, respectively. Moreover, as a clear proof of principle, the ITT system has also been used to identify cDNA encoding Stat1 in a screening assay of a large population of proteins (i.e., a plurality of proteins) which was designed to detect proteins that are capable of translocating into the nucleus upon induction by IFNγ. These results indicate that the ITT system can be used for isolating nuclear translocating proteins induced by essentially any extracellular stimuli. Thus, ITT is a useful tool for dissecting processes regulating dynamic nuclear translocation in a variety of biological systems.

In an aspect of the present invention a method is presented for identifying a polypeptide sequence capable of translocating into a cell nucleus in response to induction by an extracellular stimulus, said method comprising: (a) providing a population of cells comprising a first reporter gene encoding a first reporter polypeptide, said first reporter operably linked to a transcriptional regulatory sequence comprising a DNA binding site for a DNA-binding domain; (b) introducing into the population of cells an expression vector comprising a regulatory sequence operably linked to a nucleotide sequence encoding a fusion protein, said fusion protein comprising a polypeptide sequence, a DNA-binding (DB) domain, and a transcriptional activation (TA) domain, wherein said DB and TA domains do not confer an ability to translocate into or out of a cell nucleus; (c) dividing the population of cells of step (b) into at least two sub-populations; (d) treating a first sub-population of cells with an extracellular stimulus and treating a second population of cells with a control substance; and (e) assessing said first reporter gene expression in said first and second sub-populations of cells, wherein detecting an increase in said first reporter gene expression in said first sub-population of cells relative to that of said second sub-population of cells identifies a polypeptide sequence capable of translocating into the cell nucleus in response to the extracellular stimulus or stimuli.

Also encompassed is a method for identifying a polypeptide sequence capable of translocating out of a cell nucleus in response to induction by an extracellular stimulus, wherein in step (e) of the method detecting a decrease in said first reporter gene in said first sub-population of cells relative to that of said second sub-population of cells identifies a polypeptide sequence capable of translocating out of the nucleus in response to the extracellular stimulus or stimuli.

It is to be understood that the cell or sub-population of cells treated with an extracellular stimulus in a method of the present invention is capable of responding to the extracellular stimulus (or stimuli) used. In some aspects, any cell or population of cells may be used in the present method. In a particular embodiment of the invention, a mammalian cell or population thereof is used in a method of the present invention. Of note, some extracellular stimuli exhibit similar effects on many different types of mammalian cells, whereas other extracellular stimuli exhibit a response in a more limited spectrum of cells. Accordingly, in one aspect of the invention, a cell or cell population is used that naturally responds to an extracellular stimulus (e.g., expresses a receptor(s) for the extracellular stimulus endogenously) without genetic manipulation. In another aspect, a cell or cell population is genetically engineered to respond to an extracellular stimulus or stimuli of interest (e.g., is transfected with an expression vector encoding a receptor(s) for the extracellular stimulus or stimuli of interest).

The ITT system may be applied to any ligand-receptor system that induces nuclear translocation of signaling molecules. Exemplary ligand-receptor systems that are readily assessed using the ITT system are described herein below. The present invention is not, however, limited to those ligand-receptor systems mentioned herein, but may be used in connection with any ligand-receptor system known to a skilled practitioner. Moreover, the method may be used to determine if induction or engagement of a ligand-receptor system is capable of inducing nuclear translocation of signaling molecules.

As described herein, the first reporter gene and transcriptional regulatory sequence comprising a DNA binding site for a DNA-binding domain may be integrated into a chromosome of a cell or a cell population or maintained episomally.

In an embodiment of the present invention, the method is performed using a mammalian cell. Such cells may be isolated from a mouse, hamster, rat, rabbit, dog, cow, or primate. In a particular embodiment, a mammalian cell is a human cell. It is to be understood, however, that the method of the invention is not limited to mammalian sources. Indeed, the present method may be performed using a non-mammalian cell. Such cells include, but are not limited to, those isolated from a bacterium, yeast, fruit fly, nematode, frog, fish, or plant.

In an aspect of the present invention, the expression vector further comprises a second reporter gene encoding a second reporter polypeptide, wherein the second reporter gene is operably linked to the nucleotide sequence encoding the fusion protein.

In an aspect of the invention, the first reporter polypeptide can be a fluorescent polypeptide. In another aspect, the first or second reporter polypeptide can be a fluorescent polypeptide. In one embodiment, both the first and second reporter polypeptides are fluorescent polypeptides. To enable detection of each of the fluorescent polypeptides when co-expressed in a single cell, it is preferable that each is sufficiently distinct with respect to spectral properties and the like so as to be individually detectable when dually expressed (i.e., co-expressed). In other words, two individually detectable fluorescent polypeptides can each be detected as a distinct signal even when co-expressed. This distinction is a function of the distinct excitation/emission properties of the two fluorescent proteins. Fluorescent polypeptides useful in the practice of the present invention include, but are not limited to, green fluorescent protein (GFP), enhanced GFP (EGFP), destabilized enhanced GFP (d1EGFP), blue fluorescent protein (BFP), yellow fluorescent protein (YFP), and red fluoresent protein (RFP including DsRed2).

In another aspect of the invention, the first reporter polypeptide can be a cell surface antigen. Cell surface antigens useful in the practice of the present invention include, but are not limited to, CD2 protein, CD4 protein, and CD25 protein. These cell surface antigens can be detected using antibodies immunologically specific for a cell surface antigen in question. These antibodies can be directly conjugated with fluorescent dyes or polypeptides, or detected by secondary antibodies conjugated with fluorescent dyes or polypeptides.

In yet another aspect of the invention, the first reporter polypeptide can be a polypeptide encoded by a drug selection gene. Drug selection genes useful in the practice of the present invention include, but are not limited to, neomycin resistance gene, hygromycin resistance gene, puromycin resistance gene, and xanthine-guanine phosphoribosyltransferase (XGPRT).

In one aspect of the invention, the first reporter polypeptide is β-galactosidase (β-gal). The activity of β-gal can be detected using a luminometer, scintillation counter, or x-ray film using standard protocols.

In one aspect of the invention, a polypeptide sequence that is to be tested for the presence of a translocatable element responsive to induction by an extracellular stimulus is encoded by a nucleotide sequence from a nucleic acid library. In another aspect of the invention, a known polypeptide sequence may be tested for its ability to translocate into the nucleus in response to an extracellular stimulus. A skilled practitioner would also appreciate that fragments of a polypeptide sequence may be tested to delineate the domain(s) or site(s) of the translocatable element located in a larger polypeptide (e.g., a full length protein) of interest.

In one aspect, the method further comprises selecting for cells expressing the second reporter gene of claim 1, step (b) prior to performing step (c).

The method of the present invention may further comprise selecting for cells of said first sub-population treated with an extracellular stimulus of claim 1, step (d) expressing the first reporter gene. Also presented is a method further comprising isolating DNA from said cells of said first sub-population treated with an extracellular stimulus of claim 1, step (d) expressing the first reporter gene.

The present invention also encompasses a kit for assessing the presence of a translocatable element in a polypeptide sequence, wherein the polypeptide sequence is expressed in a cell as a component of a fusion protein, and wherein translocation mediated by said translocatable element is induced in response to an extracellular stimulus, said kit comprising: (a) an expression vector comprising a regulatory sequence operably linked to a nucleotide sequence encoding a fusion protein, wherein said nucleotide sequence encoding a fusion protein comprises a first nucleic acid sequence encoding a DNA-binding (DB) domain, a second nucleic acid sequence encoding a transcriptional activation (TA) domain, and a multiple cloning site for inserting a nucleotide sequence encoding said polypeptide sequence, wherein nucleic acid sequences encoding the DB domain, TA domain, and multiple cloning site are operably linked and polypeptides encoded therefrom are expressed in frame, and said DB and TA domains do not confer an ability to translocate into a cell nucleus, and wherein said expression vector may further comprise a second reporter gene encoding a second reporter polypeptide, said second reporter gene operably linked to said nucleotide sequence encoding said fusion protein; (b) a cell comprising a first reporter gene encoding a first reporter polypeptide, said first reporter gene operably linked to a transcriptional regulatory sequence comprising a DNA binding site for a DNA-binding domain recognized by the DB domain of the fusion protein of step (a), wherein the first reporter gene expresses the first reporter polypeptide when the fusion protein of step (a) translocates into a cell nucleus in response to the extracellular stimulus, wherein an ability to translocate into a cell nucleus in response to an extracellular stimulus is indicative of the presence of said translocatable element in said polypeptide sequence; and (c) instructions for use.

Positive control vectors for inclusion in a kit of the invention include, but are not limited to, pLGV-NLS-β-gal. Negative control vectors of the kit include, but are not limited to, pLGV, or pLGV-β-gal. Any one of pLGV-Stat1, pLG-Stat1, pLGV-Smad3 or pLG-Smad3 can be used as a negative control vector in the absence of IFNγ (pLGV-Stat1, pLG-Stat1) or TGFβ (pLGV-Smad3 or pLG-Smad3) stimulation, respectively. Such vectors can also be used as positive control vectors in the presence of IFNγ or TGFβ stimulation, respectively, if the cell line used expresses a functional IFNγ or TGFβ receptor.

A skilled practitioner would also be able to utilize a kit of the invention to detect the presence of a translocatable element in a polypeptide sequence that translocates out of the nucleus in response to an extracellular stimulus.

A kit may further comprise a reporter construct comprising a first reporter gene encoding a first reporter polypeptide, said first reporter gene operably linked to a transcriptional regulatory sequence comprising a DNA binding site for a DNA-binding domain recognized by the DB domain of the fusion protein of step (a). Useful cells for inclusion in kits of the invention are described herein. Such cells are capable of responding to the extracellular stimulus or stimuli of interest or can be genetically engineered to respond to such an extracellular stimulus or stimuli using routine procedures. Inclusion of a reporter gene construct enables a skilled practitioner to establish a reporter cell line of choice by any means known in the art, such as, for example, by transfection. Recommendations for transfection of exemplary cell lines may also be included to assist in the practice of the invention.

BRIEF DESCRIPTION OF THE DRAWINGS

FIGS. 1A-H depict the pLGV/LexA-hCD2 reporter system and results derived using this system. (FIG. 1A) pLGV expresses a fusion protein comprising LexA DB (a.a. 1-87), GFP, VP16 TA (a.a. 402-479), and a protein or polypeptide to be tested. LTR, long terminal repeat; Amp, ampicillin resistance gene; Ori, replication origin of pUC; ψ, packaging signal; and a MCS, multiple cloning site. (FIG. 1B) LexA-hCD2 reporter gene comprises 8× LexA binding elements, a minimal promoter from a mouse IFNβ gene, and the full-length cDNA of hCD2. (FIG. 1C) Cartoon of hCD2 expression induced by the fusion protein encoded by pLGV. When the LGV-fusion protein is in the cytoplasm, hCD2 is not expressed on the cell surface. If the fusion protein translocates into the nucleus when induced by ligand stimulation (an external stimulus), it binds to the LexA operators of LexA DB and activates hCD2 expression (a reporter gene). (FIGS. 1D-G) Inducible expression of hCD2 by IFNγ on BL2 cells expressing LGV-Stat1. Data for BL2 cells expressing LGV (FIG. 1D), β-gal-fusion (LGV-β-gal, control as a cytoplasmic protein) (FIG. 1E), NLS-β-gal-fusion (LGV-NLS-β-gal, control as a nuclear protein) (FIG. 1F), and LGV-Stat1 (FIG. 1G) are shown. Dotted lines: unstained control; thin line: mock-stimulation; thick line: IFNγ stimulation. (FIG. 1H) Time course of IFNγ-induced hCD2 expression in BL2 cells expressing LGV-Stat1.

FIGS. 2A-G show immunoblots revealing tyrosine-phosphorylation and nuclear translocation of LGV-Stat1 by IFNγ. (FIG. 2A) Expression of LGV-Stat1 in BL2-derived cells. Whole cell lysates (WCL) were subjected to immunoblot analysis with anti-Stat1 antibody. (FIG. 2B) IFNγ-induced tyrosine phosphorylation of LGV-Stat1 in BL2-derived cells. Cells were stimulated with IFNγ for 30 minutes, and WCL were subjected to immunoblot analysis with anti-phospho-Stat1 or anti-Stat1 antibodies. (FIG. 2C) IFNγ-induced nuclear translocation of LGV-Stat1 in BL2-derived cells. Cells were stimulated with IFNγ for 30 minutes, and nuclear extracts (NE) were subjected to immunoblot analysis with anti-Stat1 or anti-Sp1 antibodies. (FIG. 2D) NE prepared from IFNγ-treated BL2 cells expressing LGV-Stat1 and WCL prepared from unstimulated cells expressing LGV-Stat1 were subjected to immunoblot analysis with anti-LexA antibodies. (FIG. 2E) Expression of LGV-Stat1 in Stat1$^{-/-}$ mouse embryonic fibroblasts (MEF)-derived cells. WCL were subjected to immunoblot analysis with anti-Stat1 antibodies. (FIG. 2F) IFNγ-induced tyrosine phosphorylation of LGV-Stat1 in Stat1$^{-/-}$ MEF-derived cells. Cells were stimulated with IFNγ for 30 minutes, and WCL were subjected to immunoblot analysis with anti-phospho-Stat1 or anti-Stat1 antibodies. (FIG. 2G) IFNγ-induced nuclear translocation of LGV-Stat1 in Stat1$^{-/-}$ MEF-derived cells. Cells were stimulated with IFNγ for 30 minutes, and NE were subjected to immunoblot analysis with anti-Stat1 or anti-Sp1 antibodies.

FIGS. 3A-F show a pLG/LexA-d1EGFP reporter system and results derived using this system. (FIG. 3A) pLG expresses a fusion protein consisting of LexA DB (a.a. 1-87), Gal4 TA (a.a. 768-881), and a protein/polypeptide to be tested. (FIG. 3B) LexA-d1EGFP reporter gene contains 8× LexA binding elements, a mouse IFNβ minimal promoter, and d1EGFP. (FIG. 3C) Expression of LG-Smad3 in BLG-derived cells. WCL were subjected to immunoblot analysis with anti-Smad3 antibodies. (FIG. 3D) Inducible expression of GFP by TGFβ1 in BLG cells expressing LG-Smad3. BLG cells expressing LG (left panel) or LG-Smad3 (right panel) were mock-stimulated (thin line) or stimulated with TGFβ1 for 5 hr (thick line), and GFP expression was analyzed. (FIG. 3E) TGFβ1-induced nuclear translocation of LG-Smad3 in BLG-derived cells. Cells were stimulated with TGFβ1 for 1 hour, and NE were subjected to immunoblot analysis with anti-Smad3 or anti-Sp1 Ab. (FIG. 3F) NE prepared from TGFβ1-treated BLG cells expressing LG-Smad3, and WCL prepared from unstimulated BLG cells expressing LG-Smad3 were subjected to immunoblot analysis with anti-LexA antibodies.

FIGS. 4A-G illustrate the molecular cloning of Stat1 using an ITT system. (FIG. 4A) Scheme of screening of cDNA library. GFP expression in mock-stimulated (FIG. 4B) or IFNγ-stimulated (FIG. 4C) BLG cells after transduction of cDNA library, and mock-stimulated (FIG. 4D) or IFNγ-stimulated (FIG. 4E) cells after nine rounds of sorting. (FIG. 4F) IFNγ-induced GFP expression in sorted clones. Cells were mock-stimulated (thin line) or stimulated with IFNγ (thick line) for 5 hr. (FIG. 4G) Stat1 inserts amplified by genomic PCR amplification. Genomic DNAs were extracted from clones 18, 23, 44 and control cells. cDNA inserts were amplified by PCR using Stat1-specific primers. P.C. (positive control): BLG cells expressing LG-Stat1; N.C. (negative control): a sorted clone which did not show IFNγ-induced GFP expression.

DETAILED DESCRIPTION OF THE INVENTION

Figure 1H:
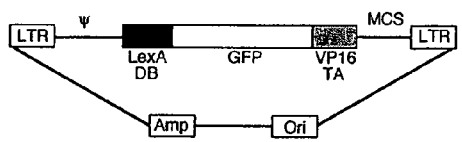
Figure 1H:
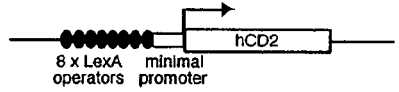
Figure 1H:
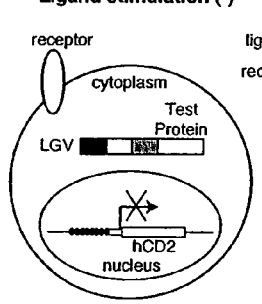
Figure 1H:
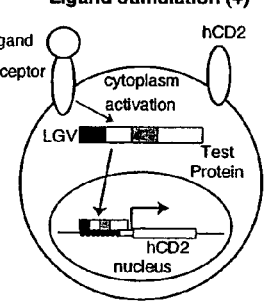
Figure 1H:
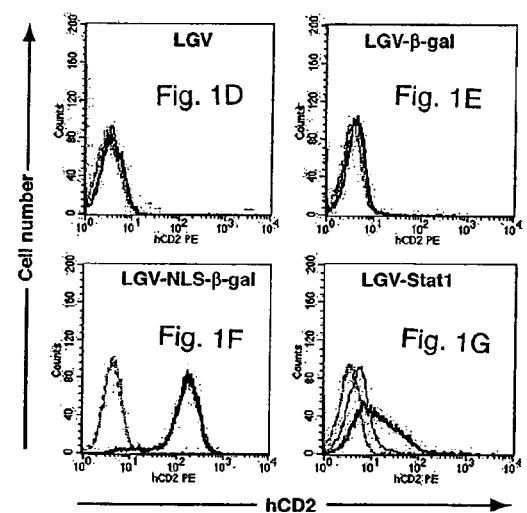
Figure 1H:
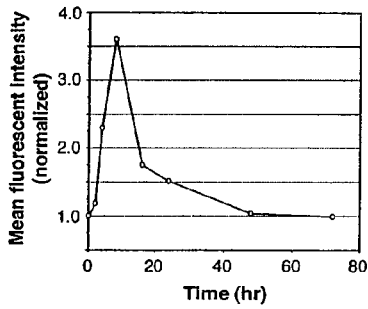

In order to more clearly set forth the parameters of the present invention, the following definitions are used:

As used in this specification and the appended claims, the singular forms "a", "an", and "the" include plural references unless the context clearly dictates otherwise. Thus for example, reference to "the method" includes one or more methods, and/or steps of the type described herein and/or which will become apparent to those persons skilled in the art upon reading this disclosure.

As used herein, the term "DNA-binding domain" refers to an amino acid sequence that binds specifically to a particular DNA sequence or sequences. The site to which the DNA-binding domain binds is known as a DNA binding site.

As used herein, the term "transcriptional activation domain" refers to an amino acid sequence that activates gene transcription when in proximity to transcriptional regulatory DNA elements of a target gene.

As used herein, a "reporter gene" means a gene whose expression can be detected or assayed by methods described herein and known in the art.

As used herein, an "extracellular stimulus or stimuli" refers to a treatment or condition to which a cell or cell population can be exposed, the source of which is outside the cell. An extracellular stimulus may refer to incubation of an intact cell in the presence of, e.g., a polypeptide, agent or compound, or exposure of an intact cell to an external condition such as, e.g., irradiation or conditions of physiological stress (e.g., heat, hypoxia, hypotonic solution). The phrase "induction by an extracellular stimulus" refers generally to cellular signals triggered in response to the extracellular stimulus.

The term "control substance", "control agent", or "control compound" as used herein refers a molecule that is inert or has no activity or negligible activity relating to an ability to modulate a biological activity. With respect to the present invention, such control substances are inert or inactive or have negligible activity with respect to an ability to modulate nuclear translocation. Exemplary controls include, but are not limited to, control media in which the cell is incubated during experimental procedures (i.e., media appropriate for the experimental procedure without the extracellular stimulus of interest) or normal media in which the cell is maintained during routine culturing (i.e., normal media without the extracellular stimulus of interest) or solutions comprising physiological salt concentrations without the extracellular stimulus of interest.

As used herein, an "interactor" or "specific binding partner" refers to a protein that is able to form a complex with another protein.

As used herein, a "translocatable element", refers to a functional unit (e.g., a polypeptide sequence) that has the potential to undergo nuclear translocation (i.e., transport into or from the nucleus). In a particular aspect of the invention, the translocation of a molecule comprising a translocatable element is induced in response to an extracellular stimulus or combination of extracellular stimuli. In a further aspect, the molecule comprising a translocatable element is a polypeptide. It is to be understood that a skilled practitioner would be capable of generating fragments of a nucleic acid sequence encoding a polypeptide comprising a translocatable element. The generation and expression of such polypeptide fragments as components of the expression vector fusion protein of the invention would facilitate the delineation of the translocatable element within the larger or full length polypeptide of interest. An analysis of amino acid sequence of the polypeptide and assessment of the domain structure/organization of the larger polypeptide via, e.g., sequence alignment with related polypeptides and/or exon-intron comparisons, may be used to determine how the larger polypeptide can be sub-divided or fragmented to further delineate the translocatable element. The nucleic acid sequence encoding the desired polypeptide fragments can then be generated by a variety of means commonly used in laboratories with expertise in molecular biology.

As used herein, the term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector.

As used herein, an increase in reporter gene expression is defined as a 1.5-fold or greater increase in expression relative to that of controls. A statistically significant decrease in reporter gene expression is defined as a 1.5-fold or greater decrease in expression relative to that of controls.

In accordance with the present invention, the DB and TA domains of the fusion protein, when considered separately or in combination, have negligible activity with respect to modulating the ability of a fusion protein to translocate into or from the nucleus. Accordingly, the phrase "said DB and TA domains do not confer an ability to translocate into a cell nucleus" refers to these domains (either individually or in combination) having negligible activity with respect to modulating the ability of a fusion protein comprising these domains to translocate into or from the nucleus.

As used herein, the phrase "assessing said first reporter gene expression" refers to a determination of first reporter gene expression. Wherein a first reporter gene encodes a detectable marker (such as, e.g., β-gal or a fluorescent polypeptide), assessing first reporter gene expression refers to detecting the expression of the detectable marker by standard means described herein and known in the art. Wherein a first reporter gene encodes a detectable marker that is a cell surface antigen, for example, assessing first reporter gene expression may refer to detecting the expression of the cell surface antigen on the surface of the cell using standard means described herein and known in the art. Wherein a first reporter gene encodes a selectable marker (such as, e.g., a drug selection gene) assessing may be used to refer to detecting reporter gene expression as reflected by the ability (or lack thereof) of a cell to survive under selection conditions indicated as useful for selecting for the particular selectable marker used.

Unless otherwise defined, all technical and scientific terms used herein have the same meaning as commonly understood by one of ordinary skill in the art to which this invention belongs. In case of conflict, however, the present application, including definitions presented herein, will control.

A novel system is described herein, which is designated the inducible translocation trap (ITT) system. It is used to advantage to identify proteins that can translocate into or out of the nucleus following signal transduction induced by an extracellular stimulus (such as, e.g., a growth factor or cytokine engaging its cell surface receptor). In a general aspect, the ITT system comprises a cDNA expression library of fusion proteins comprising a particular DNA-binding domain, the transactivation domain of a transcriptional activator, and polypeptides encoded by cDNA inserts. The cDNA expression library may be transduced into cell lines comprising a reporter gene operably linked to binding sites recognized by the DNA-binding domain, which are located in a promoter, for example, regulating expression of a reporter gene. Cells or cell lines into which such constructs are introduced may also be genetically engineered to express a receptor(s) for an extracellular stimulus or stimuli of interest or may express the receptor(s) endogenously. Pools of cells comprising the above cDNA expression library of fusion proteins and a reporter gene construct are subsequently treated with the extracellular stimulus or stimuli to trigger intracellular downstream signaling pathways. Cells expressing the reporter gene and comprising a cDNA insert encoding a polypeptide comprising a regulatory element that is responsive to the extracellular stimulus or stimuli are detected by an increase or a decrease in expression levels of the reporter gene in the presence of the extracellular stimuli. An increase or a decrease in expression levels of a reporter gene may be evaluated using a number of methods that are well known in the art, such as, e.g., flow cytometric sorting.

In one aspect, the ITT system comprises a retroviral cDNA expression library of fusion proteins comprising a LexA DNA-binding domain, the transactivation domain of a transcriptional activator, and polypeptides encoded by cDNA inserts. The retroviral library may be transduced into cell lines comprising a reporter gene operably linked to LexA-binding sites, which are located in its promoter. The cell or cell line is chosen, in part, for its ability to respond to an extracellular stimulus or stimuli of interest. Cells expressing the reporter gene and a fusion protein capable of translocating into the nucleus in response to the extracellular stimulus or stimuli utilized are detected by virtue of the induced expression of the reporter gene. As described above, an increase in reporter gene expression levels may be determined using available assays described herein and known in the art. It is to be understood that the present invention is in no way limited to the use of a retroviral expression system. A skilled artisan would be aware of numerous other expression systems that can be used to express the above-mentioned fusion proteins.

Notably, the present inventor has successfully used the ITT system to identify multiple cDNA encoding Stat1 from a cDNA library in a screen designed to detect expressed fusion proteins capable of translocating into the nucleus upon induction by IFNγ. These results demonstrate that the ITT system possesses the sensitivity to detect and isolate nuclear translocating proteins responsive to induction by extracellular stimuli. The ITT system, therefore, is a useful tool for detecting dynamic nuclear translocation of polypeptides in various biological systems.

General Information Relating to the Two-Hybrid System

A brief review of the yeast-based two-hybrid system (Fields and Song (1989) Nature 340:245), which has been used extensively to elucidate protein-protein interactions in cells, is offered herein to more clearly set forth aspects of the present invention and render apparent novel properties of the present method. As described herein, the yeast-based two-hybrid system utilizes chimeric genes and detects protein-protein interactions via the activation of reporter gene expression. Reporter gene expression occurs as a result of reconstitution of a functional transcription factor following the association of fusion proteins encoded by the chimeric genes. Typically, polynucleotides encoding two-hybrid proteins are constructed and introduced into a yeast host cell. The first hybrid protein consists of the yeast Gal4 DNA-binding domain fused to a polypeptide sequence of a known protein (often referred to as the "bait"). The second hybrid protein consists of the Gal4 activation domain fused to a polypeptide sequence of a second protein (often referred to as the "prey"). Interaction between the bait and prey proteins reconstitutes the Gal4 DNA-binding domain with the Gal4 activation domain, which leads to transcriptional activation of a reporter gene (e.g., lacZ or HIS3), which is operably linked to a Gal4 binding site.

Bait Protein: The bait fusion protein includes a fusion between a polypeptide moiety of interest (e.g., a protein of interest or a polypeptide from a polypeptide library), and a DNA-binding domain (DB domain) that specifically binds to a DNA binding site operably linked to a desired reporter gene. The nucleotide sequence encoding the polypeptide moiety of interest is cloned in-frame to a nucleotide sequence encoding the DB domain.

The basic requirements of the bait fusion protein include the ability to bind specifically to a defined nucleotide sequence (i.e., a DNA binding site) upstream of the appropriate reporter gene and operably linked thereto. The bait fusion protein should result in minimal or no transcriptional activation of the reporter gene in the absence of an interacting prey fusion protein. Consideration with regard to bait design is also desirable to avoid the generation of a bait protein wherein the ability of the DB domain to bind to its DNA binding site is impaired.

Prey Fusion Protein: The prey fusion protein includes a transcriptional activation domain (TA domain) and a candidate interactor polypeptide sequence to be tested for its ability to form an intermolecular association with the bait polypeptide. As discussed above, protein-protein interaction between the bait and prey fusion proteins (via binding of the polypeptide moiety of the bait fusion protein with the candidate interactor polypeptide sequence of the prey fusion protein) brings the DB domain of the bait fusion protein into close contact with the TA domain of the prey fusion protein, thereby generating a protein complex capable of directly activating expression of the reporter gene.

DNA sequences which encode the prey and the TA domain, e.g., a VP16 activation domain, can also include other sequences such as a nuclear localization sequence in the yeast two-hybrid system. (e.g., those derived from GAL4). A nuclear localization sequence optimizes the efficiency with which prey proteins reach the nuclear-localized reporter gene construct.

Reporter Genes: Expression of a reporter gene is indicative of a productive interaction between the prey and bait polypeptides, and facilitates the identification of cells wherein such interactions have occurred. The reporter gene sequence comprises a reporter gene operably linked to a DNA binding site to which the DNA-binding domain of the bait fusion protein binds.

A number of mammalian two-hybrid systems have been described, which operate in like manner to that detailed herein above with respect to yeast-based two-hybrid systems. See for example, U.S. Pat. No. 6,251,676, the contents of which is incorporated herein by reference in its entirety.

General Information Relating to the ITT System

The present invention is directed to a novel method that utilizes elements of the two-hybrid system. As described herein below, the elements of the two-hybrid system have, however, been rearranged and combined in a novel manner. The manner of the rearrangement and combination of these elements has created a novel system that is designed to detect and identify polypeptide sequences capable of translocating either into or from the nucleus in response to an external stimulus or stimuli. The two-hybrid system is not designed to address such an experimental purpose. In brief, the two-hybrid system is designed to detect interactions between proteins wherein the interaction coalesces components or subdomains of a transcriptional activator, namely a DB domain and TA domain, into a functional transcriptional activator. Of note, the DB and TA domains are each expressed as components of distinct polypeptides. Expression from a reporter gene, which is responsive to the transcriptional activator, serves as a means to detect the formation of a functional transcriptional activator. In contrast, the present invention comprises fusion proteins that include both the DB and TA domains, which are in turn operably linked to a polypeptide sequence, the ability of which to translocate into or out of the nucleus in response to induction by external stimuli reveals the presence of a translocatable element in the polypeptide sequence in question. The presence of a translocatable element in a polypeptide sequence that confers the ability to translocate into the nucleus is detectable by a statistically significant increase in reporter gene expression. As described herein, a statistically significant increase is defined as being $\geq$ a 1.5-fold increase in expression relative to controls (untreated by external stimuli). In embodiments wherein the present method identifies a polypeptide sequence comprising a translocatable element capable of translocating from the nucleus in response to an external stimulus or stimuli, such translocation properties are detected by a statistically significant decrease in reporter gene expression (i.e., $\geq$ a 1.5-fold decrease) relative to controls.

DNA-Binding Domains

Any polypeptide that binds to a defined DNA sequence can be used as a DNA-binding domain. The DNA-binding domain can be derived from a naturally occurring DNA-binding protein, e.g., a prokaryotic or eukaryotic DNA-binding protein. Alternatively, the DNA-binding domain can be a polypeptide derived from a protein artificially engineered to interact with specific DNA sequences. Examples of DNA-binding domains from naturally occurring eukaryotic DNA-binding proteins include p53, Jun, Fos, GCN4, or GAL4. The DNA-binding domain of the expressed fusion protein can also be generated from viral proteins, such as the papillomavirus E2 protein. In another example, the DNA-binding domain is derived from a prokaryote, e.g., the E. coli LexA repressor can be used, or the DNA-binding domain can be from a bacteriophage, e.g., a lambda cI protein. Exemplary prokaryotic DNA-binding domains include DNA-binding portions of the P22 Arc repressor, MetJ, CENP-B, Rap1, Xy1S/Ada/AraC, Bir5 and DtxR. A skilled practitioner would be aware of other DNA-binding domains that may be used to advantage in the present invention and such DNA-binding domains are encompassed herein.

A DNA-binding protein may also comprise a non-naturally occurring DNA-binding domain that is generated by combinatorial mutagenic techniques. Methods for generating novel DNA-binding proteins which can selectively bind to a specific DNA sequence are known in the art. See e.g., U.S. Pat. No. 5,198,346.

For some aspects of the invention, the DNA-binding domain used in the expressed fusion protein can comprise oligomerization motifs. It is recognized in the art that certain transcriptional regulators dimerize. Dimerization promotes cooperative binding of the transcriptional regulators to their cognate DNA binding sites. Wherein a fusion protein comprises a LexA DNA-binding domain, for example, it can further comprise a LexA dimerization domain; this optional domain facilitates efficient LexA dimer formation. Because LexA binds to its DNA binding site as a dimer, inclusion of this domain in the fusion protein also optimizes the efficiency of binding (Golemis and Brent, (1992) Mol. Cell Biol. 12:3006). Other exemplary motifs include the tetramerization domain of p53 and the tetramerization domain of BCR-ABL.

Transcriptional Activation Domains

A variety of activation domains can be used in the fusion protein. An activation domain can be a naturally occurring activation domain, e.g., an activation domain that is derived from a eukaryotic or prokaryotic source. Exemplary activation domains include VP16, GAL4, CR2, B112, or B117. The activation domain can also be derived from a virus, the VP16 activation domain, e.g., is derived from herpesvirus. The present invention is not, however, limited to those activation domains recited herein and a skilled practitioner would be aware of other activation domains that could be used in the context of the present invention.

Translocatable Elements

The polypeptide or a fragment thereof (e.g., which is or comprises a translocatable element or potentially is or comprises a translocatable element) of the fusion protein may be chosen from any protein of interest and includes proteins of unknown, known, or suspected diagnostic, therapeutic, or pharmacological importance. For example, the protein of interest can be a protein suspected of being an inhibitor or an activator of a cellular process (e.g., receptor signaling, apoptosis, cell proliferation, cell differentiation, or import or export of toxins and nutrients).

The polypeptide comprising a translocatable element can be any polypeptide, e.g., the translocatable element polypeptide can be derived from all or a portion of a known protein or a mutant thereof, all or a portion of an unknown protein (e.g., encoded by a gene cloned from a cDNA library), or a random polypeptide sequence. In the instance when the protein of interest is of a large size, e.g., has a molecular weight of over 20 kDa, it may be more convenient and experimentally feasible to use a portion of the protein.

To isolate DNA sequences encoding novel or previously unrecognized translocatable polypeptides, members of a DNA expression library (e.g., a cDNA or synthetic DNA library) can be fused in-frame to the DNA-binding domain and transcriptional activation domain to generate a library of diverse fusion proteins.

In an exemplary embodiment, a cDNA library may be constructed from an mRNA population and inserted into an expression vector. Such a library of choice may be constructed de novo using commercially available kits (e.g., from Stratagene, La Jolla, Calif.) or using well established preparative procedures (see, for example, Current Protocols in Molecular Biology, Eds. Ausubel et al. John Wiley & Sons: 1992). Alternatively, a number of cDNA libraries (from different organisms) are publicly and commercially available; sources of libraries include, e.g., Clontech (Palo Alto, Calif.) and Stratagene (La Jolla, Calif.). It is also noted that polypeptides comprising translocatable elements need not be naturally occurring full-length proteins. In certain embodiments, such polypeptides can be encoded by synthetic DNA sequences.

Sequences encoding a polypeptide or fragment thereof are cloned into the multiple cloning site of the fusion protein expression constructs of the present invention such that amino acid sequences encoded therefrom are in frame with the other components of the fusion protein such as the DB and TA domains.

Fusion Protein Vector

DNA sequences that encode a polypeptide of interest, the DB domain (e.g., a nucleic acid sequence which encodes a LexA DNA-binding domain), and TA domain (e.g., a nucleic acid sequence which encodes a VP-16 or GAL4 activation domain) are inserted into a vector such that the desired fusion protein is produced in a host cell. In that the present assay is designed to detect and identify polypeptides that are capable of translocating into the nucleus in response to an extracellular stimulus (e.g., a cytokine, growth factor, or combination thereof, an agent/compound, or treatment, such, e.g., irradiation), the DB and TA domains that are expressed as components of the fusion protein should be selected or mutated such that these domains to not include elements that could influence the ability of a fusion protein to undergo nuclear translocation. Moreover, it should be appreciated that any combination of a DB and a TA domain in a fusion protein should also be null or non-functional with respect to influencing the ability of a fusion protein to undergo nuclear translocation. Using this approach, the activity or ability of the polypeptide of interest is the controlling element with regard to responding to the extracellular stimulus or signal used.

Suitable recombinant expression vectors are known in the art, e.g., pMX retroviral vector (Onishi et al. (1996) Exp. Hematol. 24, 324-329), pM (Clontech, Palo Alto, Calif.), or pSG424 (Sadowski and Ptashne, Nucleic Acid Research, 17:7539, 1989). Preferably the recombinant expression vector includes one or more regulatory sequences operably linked to the fusion nucleic acid sequence to be expressed. The term "regulatory sequence" includes promoters, enhancers and other expression control elements (e.g., polyadenylation signals) and these sequences direct expression of the fusion protein. Other expression systems useful for expressing the above-mentioned fusion proteins are well known in the art and may be used in the present method.

In the instance where it is preferable to recover the polypeptide sequence using a bacterial host cell, as described above, the polypeptide DNA sequences are inserted into a vector that comprises an appropriate origin of replication. An appropriate origin of replication as used herein is intended to refer to an origin of replication which allows the vector to be maintained episomally and indefinitely without damaging the host cell or integrating the DNA sequence into the genomic DNA of the host cell. Since the vector is maintained episomally, the vector can be easily introduced and recovered from a bacterial host cell. An example of such a suitable origin of replication is the replication origin of pUC. Another example of a suitable origin of replication is the oriP Epstein Barr virus replication origin sequence (oriP). In a particular embodiment, a vector comprising an oriP is transformed into a mammalian cell which contains an Epstein Barr virus nuclear antigen-1 (EBNA-1). A vector comprising an oriP can replicate stably in a mammalian cell that expresses EBNA-1 (Aiyar et al., EMBO Journal, 17:12:6394-6403).

Optionally, the vector can also include a selectable marker, the expression of which in the host cell permits selection of cells comprising the marker gene from those cells that do not contain the marker gene. Selectable markers are known in the art, e.g., GFP, and nucleic acid sequences encoding proteins that confer resistance to ampicillin, neomycin, zeocin, or blasticidin.

In an embodiment of the invention, an unstructured polypeptide linker region may be introduced between the DB domain of the fusion protein and the translocatable element polypeptide sequence and/or between the TA domain and the translocatable element polypeptide sequence. The linker can facilitate, e.g., enhanced flexibility of the fusion protein allowing the DNA-binding domain to freely interact with the DNA binding site.

It will be appreciated by those skilled in the art that many variations of the fusion protein comprising the translocatable element (a polypeptide or fragment thereof), DB, and TA domains can be constructed and are considered within the scope of the present invention. For example, it will be understood that these domains can be operably linked in any arrangement that results in the productive expression of a fusion protein comprising these components. Moreover, additional elements may be included that, for example, enhance expression levels of the fusion protein, enhance sensitivity of the assay by, for example, reducing background reporter gene expression, or improve the conformation of the expressed fusion protein to enhance functionality thereof.

Exemplary ITT system fusion protein plasmids are shown in FIGS. 1A and 3A. To construct the fusion protein plasmid (pLGV) shown in FIG. 1A, a LexA DNA-binding domain [DB; amino acids (a.a.) 1-87] was fused to GFP from pEGFP-C2 (Clontech) and a VP16 transcription activation domain (TA; a.a. 402-479) and these fused components were subcloned into the pMX retroviral vector (Onishi et al. (1996) Exp. Hematol. 24, 324-329). For pLG, a LexA DB (a.a. 1-87) was fused to a Gal4 TA (a.a. 768-881), and then subcloned into pMX. For pLGV-Stat1, Stat1 cDNA was amplified by PCR, and inserted into pLGV. For pLGV-β-gal, a β-gal fragment was excised from pCMVβ (Clontech) and inserted into pLGV. For pLGV-NLS-β-gal, a nuclear localization signal (NLS) of SV40 T-antigen was chemically synthesized and inserted into pLGV-β-gal. For pLG-Smad3, a Smad3 cDNA (Kawabata et al. (1998) EMBO J. 17, 4056-4065) was inserted into pLG.

In a particular embodiment, the fusion protein vector of the present invention is maintained episomally.

Reporter Genes: Expression of the reporter gene is indicative of the presence of a fusion protein comprising a polypeptide or fragment thereof that includes a translocatable element that facilitates translocation of the fusion protein into the nucleus in response to induction by extracellular stimuli. Expression of the reporter gene enables the identification of cells expressing a fusion protein comprising such a translocatable element. The reporter gene sequence comprises a reporter gene operably linked to a DNA binding site to which the DB domain of the fusion protein binds.

In a particular embodiment of the invention, the reporter gene encodes a fluorescent molecule, e.g., an enhanced green fluorescent protein (EGFP), a green fluorescent protein (GFP) or a blue fluorescent protein (BFP). An advantage of using a reporter gene that encodes a fluorescent protein is that it enables the rapid identification and isolation of individual fluorescent positive cells. For example, using GFP as the reporter gene product, green fluorescence may be detected as early as 16 hours after transfection or transduction. Positive (fluorescent) cells can be identified using a fluorescence microscope, e.g., using an inverted phase-contrast microscope equipped with an epifluorescence light source and a fluorescein isothiocyanate filter set. Using this method, positive cells can be identified without damage to the cells, e.g., green fluorescent cells can be readily isolated using conventional cell cloning methods, such as those wherein cloning rings (e.g., small plastic cylinders) are used to isolate cells, or those wherein a conventional micropipette (such as Gilson Pipettman) is used to pick or aspirate positive cells directly. Alternatively, a fluoresence-activated cell sorter (FACS) can be used to isolate positive cells. Isolation by FACS can, however, produce a mixed population of positive clones, and hence, may cause cloning biases. It is, therefore, preferable to use a FACS which can perform single cell sorting. Total DNA from a positive clone can be prepared by standard procedures and the sequence that encodes the polypeptide comprising a translocatable element can be amplified using polymerase chain reaction (PCR) amplification and sequenced by standard procedures.

The GFP gene was originally cloned from the jellyfish *Aequorea victoria*. It encodes a protein of 238 amino acids which absorbs blue light (major peak at 395 nm) and emits green light (major peak at 509 nm) (Prasher et al., Gene 15:229-223, 1992). GPF genes and functional proteins have been identified in a variety of organisms in the phyla hydrozoa, cnidaria, anthozoa and ctenophora. Both wild-type GFP and mutated GFP from *Aequorea victoria* can be used as a reporter gene. Mutation of GFP by substitution of certain amino acids in the GFP polypeptide yields GFP proteins with improved spectral properties. For example, mutating serine 65 to a threonine generates a GFP variant which has about six-fold greater brightness than wild-type GFP (Heim et al., Nature 372:663-664, 1995). The coding sequence for such an enhanced GFP (EGFP) can be purchased commercially (Clontech, Palo Alto, Calif.). Another exemplary altered GFP is d1EGFP (destabilized enhanced GFP). In some embodiments a mammalian-optimized version of a GFP cDNA can also be used.

BPF can also be used as a reporter gene. To obtain BFP, tyrosine 66 of GFP is mutated to a histidine. This mutated GFP protein fluoresces bright blue, in contrast to the green of the wild-type protein. Other variants of GFP include yellow fluorescent protein (YFP), and cyan fluorescent protein (CFP). Other suitable fluorescent proteins include those described by Matz et al., 1999, Nature Biotechnology 17:969-973.

In another aspect of the invention, any suitable reporter gene can be used. Examples of suitable reporter genes include those that encode proteins conferring drug/antibiotic resistance to a host cell, such as the ampicillin resistance (Amp) gene. Other examples include: surface antigens, such as human CD2 (Peterson and Seed (1987), Nature 329:842-846); chloramphenicol acetyl transferase (CAT; Alton and Vapnek (1979), Nature 282:864-869), and other enzyme detection systems, such as beta-galactosidase; firefly luciferase (deWet et al. (1987), Mol. Cell. Biol. 7:725-737); bacterial luciferase (Engebrecht and Silverman (1984), PNAS 1:4154-4158; Baldwin et al. (1984), Biochemistry 23:3663-3667); phycobiliproteins (especially phycoerythrin); alkaline phosphates (Toh et al. (1989) Eur. J Biochem. 182:231-238, Hall et al. (1983) J. Mol. Appl. Gen. 2:101); or secreted alkaline phosphate (Cullen and Malim (1992) Methods in Enzymol. 216:362-368).

The amount of transcription from the reporter gene may be measured using any suitable method, which are known in the art. For example, specific RNA expression may be detected using Northern blots, or a specific protein product may be identified by a characteristic stain or an intrinsic activity.

In a particular embodiment, the protein encoded by a reporter gene is detected by an intrinsic activity associated with that protein. For instance, the reporter gene may encode a gene product that gives rise to a detectable fluorescent, colorimetric, or luminescent signal.

In other embodiments, the reporter gene provides a selection method such that cells in which the reporter gene is activated have a growth advantage. For example the reporter can enhance cell viability, e.g., by relieving a cell nutritional requirement, and/or as indicated herein above, provide resistance to a drug. Another class of useful reporter genes encodes cell surface proteins for which antibodies or ligands are available. Expression of the reporter gene allows cells to be detected or affinity purified by virtue of the expression of the surface protein.

In particular embodiments, it may be desirable to provide two or more reporter gene constructs. The simultaneous expression of the various reporter genes provides a means for distinguishing a bona fide nuclear translocation event from a spurious event (such as fusion protein cleavage) that activates the reporter gene.

The reporter gene can be maintained in a host cell episomally or can be integrated into a chromosome of the mammalian cell.

An exemplary reporter construct is LexA-hCD2 shown in FIG. 1B. This plasmid can be constructed as follows: chemically synthesized 8× LexA-binding elements and mouse IFNβ minimal promoter (Kuga et al. (1989) Nucleic Acids Res. 17, 3291) were subcloned into basic vector (Toyo Ink). LexA-binding elements plus an IFNβ minimal promoter were excised and subcloned into basic vector 2 (Toyo Ink) together with the full-length cDNA of hCD2 amplified by RT-PCR.

Another exemplary reporter construct is LexA-d1EGFP shown in FIG. 3B. This plasmid can be constructed as indicated above for LexA-hCD2, but d1EGFP (Clontech) is used instead of hCD2.

LexA-hCD2 or LexA-d1EGFP together with a hygromycin-resistance gene are transfected into Ba/F3 cells by electroporation using a Gene Pulser II system (BioRad). Hygromycin selection (0.75 mg/ml) was initiated 24 hr after transfection. Drug-resistant single colonies were obtained as described previously (Tsujino et al. (1999) Genes Cells 4, 363-373).

Host Cells: Any cultured cell can be used in the ITT system, including prokaryotic and eukaryotic cells. Exemplary eukaryotic cells include mammalian cells, such as those isolated from a mouse, hamster, rat, rabbit, dog, cow, and primate, including a human. Such cells may be isolated from a variety of tissue types known in the art.

Examples of mammalian cells and/or cell lines that can be transfected include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types.

Examples of mammalian cell lines useful for the present ITT system include, but are not limited to: murine IL-3-dependent Ba/F3 cells (Palacios et al. (1985) Cell 41, 727-734) into which the LexA-hCD2 reporter gene is transfected to establish the BL2 cell line and into which the LexA-d1EGFP gene is transfected to establish the BLG cell line.

The following is a non-limiting list of exemplary mammalian cell lines that may be used in conjunction with the ITT system. Other equally useful cell lines are known in the art and their utilization in the present invention is encompassed herein.

TABLE 1 presents a list of exemplary cell lines utilizable in the present method.

| Cell Lines | Cytokines/Growth Factors to Which the Cell Line Responds |
|---|---|
| WI-38, IMR-90 (human fibroblasts) | EGF, PDGF, insulin, IGF-I, IGF-II |
| A431 | EGF |
| PC12 | NGF |
| CTLL-2 | IL-2 |

TABLE 1-continued presents a list of exemplary cell lines utilizable in the present method.

| Cell Lines | Cytokines/Growth Factors to Which the Cell Line Responds |
|---|---|
| HepG2 | IL-6 |
| TF-1 | IL-3 |
| Jurkat | TCR signaling (eg. anti-CD3 Ab stimulation) |
| YT | IL-2 |
| NIH 3T3 | FCS |

In one aspect of the invention, the fusion protein plasmid containing an Epstein-Barr virus origin of replication (ori-P) is transfected into a mammalian cell that expresses Epstein-Barr virus nuclear antigen-1 (EBNA-1). Methods of manipulating a mammalian cell to express EBNA-1 are well known in the art. For example, the EBNA-1 sequence can be cloned into an expression vector, transfected into a mammalian cell and expressed therein. In a preferred embodiment, the mammalian cell into which the oriP fusion protein plasmid is transfected is a mammalian cell that allows the ori-P fusion protein plasmid to replicate episomally and indefinitely in the cell without causing cell death or integrating into the genomic DNA of the mammalian cell. Since such a plasmid is maintained episomally in a circular form, it can be readily introduced and recovered from a bacterial host. Use of an oriP fusion protein plasmid serves to overcome degradation problems associated with transient transfection. Normally, transiently introduced plasmids are degraded within several days in mammalian cells if there is no specific mechanism to maintain them. This period (usually 2 to 3 days) may not be long enough to isolate and purify single cell-derived colonies expressing a reporter gene. This is a practical limitation on the efficient isolation of the true positive clones that can be avoided by using the above indicated oriP system.

Methods for transfecting the DNA molecules described herein (e.g., the reporter gene and associated DNA binding sites, or DNA molecules that encode a fusion protein of the invention) into a cell can be carried out using procedures known in the art. Examples of transfection methods include calcium phosphate or calcium chloride co-precipitation, DEAE-dextran-mediated transfection, lipofection, biolistic transfer, or electroporation. Suitable methods for transfecting host cells in vitro can be found in Sambrook et al., eds., Molecular Cloning: A Laboratory Manual (2nd ed., Cold Spring Harbor Laboratory Press, Cold Spring Harbor, N.Y., 1989) and other laboratory manuals. In a particular embodiment, cells are transfected by electroporation using a Gene Pulser II System (BioRad). Virus-based constructs or systems also facilitate introduction of DNA molecules via infection/transduction.

Ligand-receptor systems: As indicated herein above, the ITT system may be applied to any ligand-receptor system that induces nuclear translocation of signaling molecules. The following is a non-limiting list of exemplary ligand-receptor systems that may be assessed using the ITT system. The list presents only one or two examples for each of the receptor family members. It is to be understood that related family members are also encompassed herein.

TABLE 2 presents a list of exemplary ligand-receptor systems assayable using the method of the present invention.

| Receptor Family | Examples of Ligands | Receptor |
|---|---|---|
| Type I cytokine receptors: | interleukin 2 (IL-2) | IL-2 receptor (IL-2R) |
| Type II cytokine receptors: | IFNγ | IFNγR |
| Antigen receptors and co-receptors: | extracellular pathogens | B cell receptor (BCR) |
| | MHC + antigenic peptides | T cell receptor (TCR) |
| | B7.1 | CD28 |
| Toll-like receptors: | lipopolysaccharide (LPS) | TLR4 complex |
| G-protein coupled receptors (GPCR): | | |
| chemokine receptors | CCL5 | CCR5 |
| neurotransmitters | acetylcholine (Ach) | muscarinic AchR |
| Adhesion molecule receptors: | ICAM-1 | LFA-1 (integrinα/β) |
| TNF (tumor necrosis factor) receptor family: | Fas ligand | Fas |
| TGFβ receptor family: | TGFβ1 | TGFβR |
| Viruses: | HIV | CD4 + CCR5 |
| Radiation: | γ-ray | DNA repair machinery |

A skilled artisan would, however, be aware of numerous other ligand-receptor systems that may be examined using a method of the present invention. The present invention is, therefore, not limited to those ligand-receptor systems mentioned herein, but may be used in connection with any ligand-receptor system.

Screening Assays: The ITT system can be used to screen for agents capable of acting as agonists or antagonists of nuclear translocation of a particular protein or proteins. In general, the assay evaluates the ability of an agent to modulate nuclear translocation of a polypeptide determined to be capable of such translocations. Exemplary agents include peptides, nucleic acids, carbohydrates, small organic molecules, and natural product extract libraries, such as those isolated from animals, plants, fungus and/or microbes.

In an exemplary screening assay of the present invention, the methods described herein can be used to determine if an agent of interest can modulate nuclear translocation of a polypeptide determined to be capable of such translocations. The ability of the agent to modulate the nuclear translocation is determined by assessing an increase or decrease in reporter gene expression, e.g., expression of a fluorescent protein, such as GFP. Wherein a decrease in reporter gene expression in the presence of an agent of interest is detected as compared to a control cell, the agent is predicted to inhibit nuclear translocation. Alternatively, wherein an agent causes an increase in reporter gene expression in the presence of the agent, as compared to a control cell, the agent is predicted to enhance nuclear translocation. In the control cell, expression of the reporter gene is determined in the absence of an agent of interest. Executing appropriate controls when performing such experiments is essential so as to avoid conclusions that are based on artifact. Skilled practitioners are well versed in designing experiments having appropriate controls. Moreover, appropriate controls are also described herein.

The present invention can also be used to screen for agents that are useful for regulating gene expression in vitro and in vivo. For example, an agent of interest can be tested for its ability to modulate nuclear translocation of a polypeptide known to participate in a signaling cascade that results in altered expression levels of a target gene. Identification of an agent that enhances nuclear translocation the polypeptide, for example, as evidenced by increased reporter gene expression, identifies an agent capable of modulating the expression of a downstream target gene.

Kit: The invention provides a kit for detecting interaction between a fusion protein comprising a polypeptide of interest and a reporter construct localized to the cell nucleus and responsive thereto. In an illustrative embodiment, the kit includes at least one fusion protein construct and a reporter gene construct and/or a host cell comprising a reporter gene construct. In a preferred embodiment, the kit includes: (a) a fusion protein construct/expression vector comprising a regulatory sequence operably linked to a nucleotide sequence encoding a DNA-binding domain, a cloning site (e.g., a convenient cloning site which contains a unique restriction site or a multiple cloning site) for inserting a nucleotide sequence which encodes a polypeptide that may be evaluated for its ability to translocate into or out of the nucleus in response to an extracellular stimulus (the functional properties of such polypeptides with regard to nuclear translocation may be known or unknown), which in turn is operably linked to a nucleotide sequence encoding a transcriptional activation domain. The nucleotide sequence that encodes the polypeptide is expressed in frame with the DNA-binding domain and the transcriptional activation domain. The fusion protein construct may further include an origin of replication sequence and/or a reporter gene encoding a reporter polypeptide distinguishable from that of the reporter gene construct. The kit also includes (b) a reporter gene construct which contains a sequence encoding a reporter polypeptide (such as, e.g., a fluorescent polypeptide) operably linked to a transcriptional regulatory sequence comprising a DNA binding site for the DNA-binding domain of the fusion protein encoded by construct (a); (c) optionally, a cell line comprising a reporter gene construct which comprises a sequence encoding a reporter polypeptide (such as, e.g., a fluorescent polypeptide) operably linked to a transcriptional regulatory sequence comprising a DNA binding site for the DNA-binding domain of the fusion protein encoded by construct (a); and (d) instructions for use. In a particular embodiment, the reporter gene is integrated into the chromosome of a cell (such as, e.g., a eukaryotic or prokaryotic cell).

The kit can also include primers, which can be used to amplify the polypeptide sequence comprising a translocatable element. Optionally, the kit may also include bacterial cells into which one can introduce total DNA from a mammalian cell that was identified to comprise a polypeptide that translocated into the nucleus in response to a particular extracellular stimulus. A kit may also optionally comprise positive control fusion constructs (e.g., LG-Smad3) that have been shown to activate reporter gene expression in response to a defined extracellular stimuli (e.g., TGFβ1).

Other Uses for the Methods Described Herein: The methods described herein can be used for a variety of different purposes, e.g., for identifying proteins that translocate into the nucleus in response to a particular extracellular signal and are, therefore, components of a signal transduction pathway that initiates at the cell surface and is transmitted into the nucleus, for identifying components of a signal transduction pathway, for assigning functionality to a previously uncharacterized polypeptide, for identifying therapeutic targets, and/or for general cloning strategies.

Alternatively, the methods described herein can be used to map residues of a protein involved in nuclear localization. Thus, for example, various forms of mutagenesis can be utilized to generate a combinatorial library of a polypeptide found to comprise a translocatable element, and the ability of the corresponding fusion protein to translocate into the nucleus in response to an appropriate extracellular signal can be assayed.

Methods commonly known in the art of recombinant DNA technology which can be used in the present invention are described in Ausubel et al. (eds.), 1993, Current Protocols in Molecular Biology, John Wiley & Sons, NY; and Kriegler (1990) Gene Transfer and Expression, A Laboratory Manual, Stockton Press, NY.

Although methods and materials similar or equivalent to those described herein can be used in the practice or testing of the invention, preferred methods and materials are described below. The materials, methods, and examples are illustrative only and not intended to be limiting. Other features and advantages of the invention will be apparent from the detailed description and the claims.

EXAMPLE I

Methods and Materials

Plasmid Construction

For construction of the LexA-hCD2 reporter gene, chemically synthesized 8× LexA-binding elements and mouse IFNβ minimal promoter (Kuga et al. (1989) Nucleic Acids Res. 17, 3291) were subcloned into basic vector (Toyo Ink). Basic vector is also known as PicaGene Basic Vector (PGV-B; a complete DNA sequence of which is presented in SEQ ID NO: 5. LexA-binding elements plus IFNβ minimal promoter were excised and subcloned into basic vector 2 (Toyo Ink) together with the full-length cDNA of hCD2 amplified by RT-PCR. Basic vector 2 is also referred to as PicaGene Basic Vector 2 (PGV-B2; see SEQ ID NO: 6 for a complete DNA sequence). For LexA-d1EGFP, d1EGFP (Clontech) was used instead of hCD2. LexA-hCD2 or LexA-d1EGFP together with a hygromycin-resistance gene was transfected into Ba/F3 cells by electroporation using a Gene Pulser II system (BioRad). Hygromycin selection (0.75 mg/ml) was initiated 24 hr after transfection. Drug-resistant single colonies were obtained as described previously (Tsujino et al. (1999) Genes Cells 4, 363-373).

For construction of pLGV, a LexA DNA-binding domain [DB; amino acids (a.a.) 1-87] was fused to GFP from pEGFP-C2 (Clontech) and a VP16 transcription activation domain (TA; a.a. 402-479). These components were subcloned into the pMX retroviral vector (Onishi et al. (1996) Exp. Hematol. 24, 324-329). For pLG, a LexA DB (a.a. 1-87) was fused to a Gal4 TA (a.a. 768-881), and then subcloned into pMX. For pLGV-Stat1, Stat1 cDNA was amplified by PCR, and inserted into pLGV. For pLGV-β-gal, a β-gal fragment was excised from pCMVβ (Clontech) and inserted into pLGV. For pLGV-NLS-β-gal, a nuclear localization signal (NLS) of SV40 T-antigen was chemically synthesized and inserted into pLGV-β-gal. For pLG-Smad3, a Smad3 cDNA (Kawabata et al. (1998) EMBO J. 17, 4056-4065) was inserted into pLG.

All chemically synthesized and PCR-derived DNA sequences were verified by DNA sequencing.

Cytokine Stimulation

Murine IFNγ (10 ng/ml) and human TGFβ1 (2 ng/ml) were used. Recombinant cytokines were purchased from R & D Systems.

Preparation of cDNA Library

Poly(A)+ RNA was prepared from Ba/F3 cells using a Poly(A) Quick mRNA isolation kit (Stratagene). A unidirectional cDNA library was constructed using a Superscript Plasmid System (Invitrogen) and an EcoR I adaptor (New England Biolabs). Double-stranded cDNAs were synthesized from 7 μg of mRNA and size-fractionated through 1% agarose gel, and cDNAs larger than 500 bp were cloned into the EcoR I-Not I site of pLG (100 ng). The ligated DNA was transformed into ElectroMax DH10B electrocompetent cells (Invitrogen). The cDNA library comprised 3×10$^6$ clones, >95% of which had cDNA insertions with an average size of 1.2 kilobase pairs (kbp).

Flow Cytometry

For detection of hCD2, cells were treated with phycoerythrine-conjugated monoclonal antibodies (Leu-5b, BD Biosciences) for 30 minutes at 4° C. After washing, the stained cells were analyzed by FACS Caliber or FACScan Flowcytometer (BD Biosciences). An Epics Elite (Epics) or MoFlow (Cytomation) cell sorter was used for cell sorting. Expression levels of hCD2 and GFP were quantified using FlowJo software (Tree Star).

Genomic PCR and DNA Sequencing

To obtain integrated cDNAs from the genome of sorted clones, genomic DNA was subjected to PCR with upstream (5'-CAATGGATGATGTATATAACTATCTATTCGAT-3'; SEQ ID NO: 1) and downstream (5'-TCCCCCTTTTTCTGGAGACTAAATAAAAT-3'; SEQ ID NO: 2) retroviral vector primers. The PCR was run for 30 cycles [30 seconds (sec) at 94° C., 2 sec at 57.4° C., and 2 minutes (min) at 70° C.] with KOD XL DNA polymerase (Novagen). The PCR fragments cloned into pLG were sequenced with the upstream retroviral vector primer. For amplification of Stat1, PCR primers 5'-ACAGGATCCATGT-CACAGTGGTTCGAGCTTCAG-3' (SEQ ID NO: 3) and 5'-CGGGTCGACGTGTTTATACTGTGCTCAT-CATACTGTC-3' (SEQ ID NO: 4) were used.

Immunoblot Analysis

Preparation of nuclear extract (NE) and whole cell extract (WCL) and immunoblot analyses were performed as previously described (Sato et al. (1998) FEBS Letters 425, 112-116; Tsujino et al. (2000) Proc. Natl. Acad. Sci. USA 97, 10514-10519). The antibodies used in the present study are as follows: anti-phospho-Stat1, anti-Sp1 (Santa Cruz Biotechnology), anti-Stat1, anti-LexA (Upstate Biotechnology), and anti-Smad2/3 (BD Biosciences).

Results

Detection of Nuclear Translocation by Reporter Gene Expression

The present method, which is directed to the identification of molecules that translocate into the nucleus when induced by extracellular stimuli, is summarized in FIG. 1. The strategy is based on expression of a fusion protein comprising a LexA DNA-binding domain (LexA DB) (a.a. 1-87), a VP16 transactivation domain (VP16 TA) (a.a. 402-479), and a test protein encoded by cDNA subcloned downstream of VP16 TA (pLGV vector, FIG. 1A). Green fluorescent protein (GFP) was inserted between LexA DB and VP16 TA as a marker of expression of the fusion protein. The fusion molecule is expressed in cells comprising a hCD2 reporter gene having multiple LexA-binding sites in its promoter (LexA-hCD2) (FIG. 1B). Following nuclear translocation of the fusion protein by ligand stimulation, the LexA DB targets the fusion protein to the LexA operator sites of the reporter gene, then the VP16 TA activates the expression of hCD2 (FIG. 1C). Thus, nuclear translocation of the test protein is detected by the expression of hCD2.

To examine whether ligand-induced nuclear translocation can be detected with this system, the IFNγ-Stat1 system wherein IFNγ induces nuclear translocation of Stat1 (Stark et al. (1998) Annu. Rev. Biochem. 67, 227-264; Levy et al. (2002) Nat. Rev. Mol. Cell Biol. 3, 651-662) was chosen for evaluation. Mouse Stat1 cDNA (Zhong et al. (1994) Proc. Natl. Acad. Sci. USA 91, 4806-4810) was inserted into pLGV to express LexA DB-GFP-VP16 TA-Stat1 fusion protein (LGV-Stat1). As a cytoplasmic control molecule, β-galactosidase (β-gal) cDNA was fused to pLGV to express LGV-β-gal, which is predicted to be in the cytoplasm (Adachi et al. (1999) EMBO J. 18, 5347-5358). As a nuclear control molecule, the nuclear localization signal (NLS) of SV40 T-antigen (Kalderon et al. (1984) Cell 39, 499-509) was fused in front of β-gal to express LGV-NLS-β-gal, which should reside in the nucleus. LexA-hCD2 reporter gene was transfected into murine IL-3-dependent Ba/F3 cells (Palacios et al. (1985) Cell 41, 727-734) to establish a BL2 cell line utilizable in the present method. Notably, Stat1 is activated by IFNγ in Ba/F3-derived cells (Fujii et al. (1995) Proc. Natl. Acad. Sci. USA 92, 5482-5486). Retroviral gene transfer into BL2 cells is achieved as previously described (Kitamura et al. (1995) Proc. Natl. Acad. Sci. USA 92, 9146-9150; Kamijo et al. (1997) Cell 91, 649-659).

As shown in FIG. 1D, BL2 cells expressing LGV do not express hCD2, either in the absence or presence of IFNγ, indicating that LGV is too large to translocate into the nucleus by simple diffusion. Expression of hCD2 is not observed on BL2 cells expressing LGV-β-gal either in the absence or presence of IFNγ (FIG. 1E). In contrast, BL2 cells expressing LGV-NLS-β-gal expressed hCD2 in the absence and presence of IFNγ (FIG. 1F). These results suggest that hCD2 expression faithfully reflects nuclear localization of the test proteins. When LGV-Stat1 is expressed in BL2 cells, low background expression of hCD2 is detected in the absence of IFNγ (FIG. 1G). In contrast, significant up-regulation of hCD2 is observed 7 hours after IFNγ stimulation. These results demonstrate that this system enables detection of ligand-induced nuclear translocation of signaling molecules as indicated by expression of hCD2. It has been shown that the N-terminal domain of Stat1 is essential for IFNγ-induced nuclear translocation of Stat1 (Strehlow et al. (1998) J. Biol. Chem. 273, 28049-28056). In agreement with this observation, the present inventor found that IFNγ stimulation could not induce expression of hCD2 on BL2 cells expressing a mutant form of Stat1 lacking the N-terminal 131 a.a. residues, further suggesting that translocation of LGV-Stat1 depends on nuclear import machinery of endogenous Stat1 protein. Examination of the kinetics of hCD2 induction by IFNγ in BL2 cells expressing LGV-Stat1 revealed that expression of hCD2 peaks at 8 hours after IFNγ stimulation, and is down-regulated to basal levels by 72 hours after stimulation (FIG. 1H).

To evaluate inhibitory effects of the LGV appendage on translocation of the fused protein, tyrosine-phosphorylation levels and nuclear translocation of LGV-Stat1 were examined. As shown in FIGS. 2B and 2C, LGV-Stat1 is phosphorylated on tyrosine residues and translocates into the nucleus in response to IFNγ treatment of BL2 cells expressing LGV-Stat1. Extra bands with smaller molecular weights (MW) are not detected in the nuclear extracts (NE) isolated from IFNγ-treated cells using anti-LexA antibody (Ab) (FIG. 2D), excluding a possibility that hCD2 induction is caused by non-physiological processing such as a cleavage of the fusion protein. IFNγ-induced tyrosine-phosphorylation and nuclear translocation of LGV-Stat1 is also detected in Stat1$^{-/-}$ mouse embryonic fibroblasts (MEF) wherein LGV-Stat1 is expressed (Durbin et al. (1996) Cell 84, 443-450) (FIGS. 2F and 2G). These results show that IFNγ-induced dimerization and nuclear translocation of LGV-Stat1 occur in the absence of endogenous Stat1, indicating that fusion with LGV does not adversely affect dimerization and nuclear translocation of Stat1.

Screening of cDNA Library Using ITT

A modified system for screening cDNA libraries to isolate nuclear translocating molecules is also described herein. This system consists of a pLG retroviral vector that expresses cDNA sequences fused to LexA DB (a.a. 1-87) and Gal4 TA (a.a. 768-881) (FIG. 3A) and LexA-d1EGFP (destabilized enhanced GFP) reporter gene (FIG. 3B). Incorporation of a GFP reporter into the screening system renders staining of the cells in preparation for flow cytometry unnecessary. A LexA-d1EGFP gene was transfected into Ba/F3 cells to establish a BLG cell line useful for the present method. Of note, Stat1 fused with LexA DB-Gal4 TA (LG-Stat1) activates expression of GFP in BLG cells by IFNγ, and IFNγ-induced GFP expression in cells expressing LG-Stat1 reaches a peak 4 hours after stimulation and is down-regulated to basal levels within 24 hours after stimulation.

To examine whether the modified system can detect ligand-induced nuclear translocation of different families of transcription factors, an LG-fusion protein of Smad3, which translocates into the nucleus when induced by TGFβ (Massagué. (2000) Nat. Rev. Mol. Cell Biol. 1, 169-178; Miyazono et al. (2000) Adv. Immunol. 75, 115-157), was constructed. Ba/F3 cells respond to TGFβ1 (Mahmud et al. (1999) Br. J. Haematol. 105, 470-477). Human Smad3 cDNA (Kawabata et al. (1998) EMBO J. 17, 4056-4065) is inserted into pLG to express LG-Smad3. BLG cells are transduced with LG-Smad3 and cloned by single-cell sorting. Expression of LG-Smad3 is examined by immunoblot analysis with anti-Smad3 Ab (FIG. 3C). Each clone expressing LG-Smad3 is stimulated with TGFβ1 for 5 hours, and expression of GFP is analyzed. Expression of GFP is not detected in BLG cells expressing LG, either in the absence or presence of TGFβ1 (FIG. 3D, left panel). In contrast, TGFβ1 stimulation induces expression of GFP in BLG cells expressing LG-Smad3 (FIG. 3D, right panel). Up-regulation of GFP by TGFβ1 is observed in all clones expressing LG-Smad3 tested. The present inventor has thus confirmed that LG-Smad3 translocates into the nucleus in response to TGFβ1 signaling (FIG. 3E). Extra bands with smaller MW are not detected with anti-LexA Ab (FIG. 3F), excluding a possibility that GFP induction is caused by non-physiological processing such as a cleavage of the fusion protein. TGFβ1 also induces GFP expression in BLG cells expressing LG-Smad2 and hCD2 expression in BL2 cells expressing LGV-Smad2 or LGV-Smad3. In that the ITT system is shown herein to be effective for examining nuclear translocation events of such diverse systems as those involving IFNγ-Stat1 and TGFβ-Smad2/3, it is apparent that the ITT system is an effective tool for analyzing nuclear translocation of molecules implicated, or potentially implicated, in signaling pathways in general.

The present inventor also demonstrates herein that the ITT system can be used to isolate cDNAs capable of translocating into the nucleus in response to IFNγ treatment from a complex cDNA library. To this end, a cDNA library is constructed from poly(A)+ RNA isolated from Ba/F3 cells comprising a pLG vector. Screening of the cDNA library is performed as schematically depicted in FIG. 4A. 24 μg of the cDNA library is transfected into $9 \times 10^6$ of 293T cells using an ecotropic helper plasmid to produce retrovirus particles. Then, $3 \times 10^7$ of BLG cells were infected with the supernatant (30 ml) of the 293T cells comprising virus particles. Infection efficiency is estimated to be about 10% in this experimental condition. Two days after infection, cells are stimulated with IFNγ for 4 hours, and GFP (+) cells are sorted by flow cytometry. Sorted cells are incubated for two days to achieve down-regulation of GFP and expansion of the sorted cells, then GFP (−) cells are sorted from the cell pool. Nine rounds of GFP (+) sorting after IFNγ stimulation and subsequent GFP (−) sorting are performed. As shown in FIGS. 4B and 4C, IFNγ stimulation only marginally increases the percentage of GFP (+) cells just after infection (mock-stimulation, 3.19%; IFNγ stimulation, 3.51%). In contrast, after nine rounds of sorting, IFNγ stimulation markedly increases GFP (+) cells in sorted cell populations (mock-stimulation, 8.26%; IFNγ stimulation, 23.9%) (FIGS. 4D and 4E). After nine rounds of sorting, cells are subjected to single-cell sorting, and GFP expression is examined in the presence or absence of IFNγ for each clone. Representative data for clones which reveal induction of GFP expression by IFNγ are shown in FIG. 4F. Genomic DNAs extracted from these clones are used as templates for PCR amplification using viral vector primers. The amplified PCR fragments are sequenced and 87 out of 101 clones are identical to Stat1 cDNA. Genomic DNAs extracted from these clones gave rise to a common 2.3-kbp band after PCR amplification using Stat1 primers (FIG. 4G, representative data from three clones are shown). These data demonstrate that the ITT system can be used for isolation of polypeptides capable of translocating to the nucleus in response to extracellular stimuli.

Discussion

Translocation of signaling molecules from the cytoplasm to the nucleus is a critical step for signal transduction from cell surface receptors. Prior to the ITT system of the present invention, however, no systematic methods had been reported to identify nuclear translocating molecules induced by extracellular stimuli. This is, in part, due to the complexities (e.g., diverse mechanisms) involved in the different signaling pathways that lead to nuclear translocation of downstream signaling molecules (Cyert. (2001) J. Biol. Chem. 276, 20805-20808; Brivanlou et al. (2002) Science 295, 813-818). By combining reporter gene expression as an assay for nuclear translocation (Struhl et al. (1998) Cell 93, 649-660; Ueki et al. (1998) Nature Biotech. 16, 1338-1342; Rhee et al. (2000) Nature Biotech. 18, 433-437) with flow cytometric detection of reporter expression, the present inventor has succeeded in detecting transient nuclear translocation of signaling molecules. Because ITT uses a reporter gene expression as an assay for nuclear translocation, it does not assume a priori a potential mechanism of nuclear translocation and, therefore, can be applied to the analysis of signaling pathways from any cell surface receptors.

As shown herein, the reporter hCD2 expression faithfully reflects subcellular localization of the test proteins (FIG. 1). The cytoplasmic β-gal fused to LGV failed to induce expression of hCD2 reporter gene either in the absence or presence of IFNγ (FIG. 1E). In contrast, when an NLS is inserted between LGV and β-gal, expression of the fusion molecule causes increased expression of hCD2, consistent with the expected nuclear localization of the fusion molecule (FIG. 1F). When an LGV-Stat1 fusion molecule is expressed in BL2 cells, low background expression of hCD2 is detected in the absence of IFNγ (FIG. 1G). The background expression of hCD2 in the absence of IFNγ can be explained by ligand-independent nuclear translocation of Stat1 (Kumar et al. (1997) Science 278, 1630-1632). In contrast, significant up-regulation of hCD2 expression is induced by IFNγ (FIG. 1G). These results show that localization of a test molecule can be monitored by expression of a hCD2 reporter gene and that ligand-induced nuclear translocation can be detected as up-regulation of the reporter gene by, for example, flow cytometry. The present inventor believes that this is the first report to show that reporter gene expression can be used to detect inducible nuclear translocation in mammalian cells. As shown in FIG. 2, LGV-Stat1 is tyrosine-phosphorylated and translocated into the nucleus in response to induction by IFNγ, when expressed in BL2 cells, as well as in Stat1$^{-/-}$ MEFs. These data demonstrate that fusion with LGV does not severely affect dimerization and nuclear translocation of Stat1.

The present system can also be used to detect ligand-induced nuclear translocation of Smad transcription factors that translocate into the nucleus in response to induction by TGFβ (FIG. 3D). Thus, the ITT system works not only for the IFNγ-Stat1 system, which is mediated by tyrosine-phosphorylation, but also for the TGFβ-Smad2/3 system, which is mediated by serine-phosphorylation. These results demonstrate that the ITT system is robust and of utility for a broad variety of applications involving diverse signaling pathways.

The ITT system is also shown herein to be useful for screening a viral expression cDNA library to isolate cDNA molecules encoding proteins that translocate from the cytoplasm to the nucleus in response to extracellular signaling molecules (e.g., cytokines, growth factors, and the like) that bind to cell surface receptors. In a screening assay designed to detect/identify IFNγ-induced nuclear translocating proteins from a cDNA library, the present inventor was able to isolate Stat1 cDNA, a molecule whose nuclear translocation is known to be induced as a consequence of IFNγ signaling pathways (FIG. 4). Indeed, the majority of the cDNA inserts recovered from sorted clones are Stat1, consistent with the fact that Stat1 plays a major role in IFNγ signaling (Stark et al. (1998) Annu. Rev. Biochem. 67, 227-264; Levy et al. (2002) Nat. Rev. Mol. Cell Biol. 3, 651-662). Thus, the ITT system can be used for isolation of nuclear translocating proteins induced by extracellular stimuli and is, therefore, well applied to the screening of, for example, cDNA and/or EST libraries.

In addition to elucidation of nuclear import induced by activation of cell surface receptors as described above, this system has other applications. For example, this system may be applied to dissection of signaling processes such as those triggered by exposure to ultraviolet light or γ-ray irradiation, neither of which is thought to be mediated by specific cell surface receptors. In addition, by selecting cells in which reporter gene expression is down-regulated by extracellular stimuli in screening of a cDNA library, ITT may also enable detection of proteins which are inducibly exported from the nucleus in response to such stimuli, such as histone deacetylases HDAC4 and HDAC5 (McKinsey et al. (2000) Nature 408, 106-111). Furthermore, the ITT reporter system may be used to identify extracellular signaling molecules which induce nuclear translocation of molecules of interest. Thus, ITT is a useful tool for analyzing dynamic translocation of proteins in various biological systems.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for identifying a polypeptide sequence capable of translocating into a cell nucleus in response to induction by an extracellular stimulus, said method comprising:
   (a) providing a population of cells comprising a first reporter gene encoding a first reporter polypeptide, said first reporter gene operably linked to a transcriptional regulatory sequence comprising a DNA binding site for a DNA-binding domain;
   (b) introducing into the population of cells an expression vector comprising a regulatory sequence operably linked to a nucleotide sequence encoding a fusion protein, said fusion protein comprising a polypeptide sequence, said DNA-binding (DB) domain, and a transcriptional activation (TA) domain, wherein said DB and TA domains do not confer an ability to translocate into a cell nucleus, and wherein binding of said DB domain of said fusion protein to said transcriptional regulatory sequence operably linked to said first reporter gene activates transcription of said first reporter gene;
   (c) dividing the population of cells of step (b) into at least two sub-populations;
   (d) treating a first sub-population of cells with an extracellular stimulus, wherein said extracellular stimulus induces translocation of said fusion protein if said polypeptide sequence of said fusion protein comprises a translocatable element responsive to said extracellular stimulus, and treating a second population of cells with a control substance; and
   (e) assessing said first reporter gene expression in said first and second sub-populations of cells, wherein detecting an increase in said first reporter gene expression in said first sub-population of cells relative to that of said second sub-population of cells identifies the polypeptide sequence capable of translocating into the cell nucleus in response to said extracellular stimulus, wherein said first reporter gene expression is transcriptionally activated by binding of said DB domain of said fusion protein to said transcriptional regulatory sequence operatively linked to said first reporter gene following translocation of said fusion protein into the nucleus.

2. The method of claim 1, wherein the first reporter gene and transcriptional regulatory sequence are integrated into a chromosome of said population of cells or maintained episomally.

3. The method of claim 1, wherein said expression vector further comprises a second reporter gene encoding a second reporter polypeptide, said second reporter gene operably linked to said nucleotide sequence encoding said fusion protein.

4. The method of claim 1, wherein the population of cells is a mammalian cell population.

5. The method of claim 4, wherein the mammalian cell population is a human cell population.

6. The method of claim 1, wherein the first reporter polypeptide is a fluorescent polypeptide.

7. The method of claim 3, wherein the first or second reporter polypeptide is a fluorescent polypeptide.

8. The method of claim 3, wherein the first reporter polypeptide is a first fluorescent polypeptide and the second reporter polypeptide is a second fluorescent polypeptide, wherein each of said first and second fluorescent polypeptides is detectable as a distinct signal when co-expressed in a cell.

9. The method of claim 6, wherein the fluorescent polypeptide is a green fluorescent protein (GFP), an enhanced GFP (EGFP), a destabilized enhanced GFP (d1EGFP), a blue fluorescent protein (BFP), a yellow fluorescent protein (YFP), or a red fluoresent protein (RFP including DsRed2).

10. The method of claim 8, wherein either of the fluorescent polypeptides is a green fluorescent protein (GFP), an enhanced GFP (EGFP), a destabilized enhanced GFP (d1EGFP), or a blue fluorescent protein (BFP).

11. The method of claim 1, wherein the polypeptide sequence is encoded by a nucleotide sequence from a nucleic acid library.

12. The method of claim 3, further comprising selecting for cells expressing the second reporter gene of step (b) prior to performing step (c).

13. The method of claim 1, wherein said assessing further comprises selecting for cells of said first sub-population treated with an extracellular stimulus of step (d) expressing the first reporter gene.

14. The method of claim 13, further comprising isolating DNA from said cells of said first sub-population treated with an extracellular stimulus of step (d) expressing the first reporter gene.

15. A method for identifying a polypeptide sequence capable of translocating out of a cell nucleus in response to induction by an extracellular stimulus, said method comprising:
   (a) providing a population of cells comprising a first reporter gene encoding a first reporter polypeptide, said first reporter gene operably linked to an transcriptional regulatory sequence comprising a DNA binding site for a DNA-binding domain;
   (b) introducing into the population of cells an expression vector comprising a regulatory sequence operably linked to a nucleotide sequence encoding a fusion protein, said fusion protein comprising a polypeptide sequence, said DNA-binding (DB) domain, and a transcriptional activation (TA) domain, wherein said DB and TA domains do not confer an ability to translocate into a cell nucleus, and wherein binding of said DB domain of said fusion protein to said transcriptional regulatory sequence operably linked to said first reporter gene activates transcription of said first reporter gene;
   (c) dividing the population of cells of step (b) into at least two sub-populations;
   (d) treating a first sub-population of cells with an extracellular stimulus, wherein said extracellular stimulus induces translocation of said fusion protein if said polypeptide sequence of said fusion protein comprises a translocatable element responsive to said extracellular stimulus, and treating a second population of cells with a control substance; and
   (e) assessing said first reporter gene expression in said first and second sub-populations of cells, wherein detecting a decrease in said first reporter gene expression in said first sub-population of cells relative to that of said second sub-population of cells identifies the polypeptide sequence capable of translocating out of the cell nucleus in response to said extracellular stimulus, wherein said first reporter gene expression is transcriptionally activated by binding of said DB domain of said fusion protein to said transcriptional regulatory sequence operatively linked to said first reporter gene prior to translocation of said fusion protein out of the nucleus.

16. The method of claim 15, wherein the first reporter gene and transcriptional regulatory sequence are integrated into a chromosome of said population of cells or maintained episomally.

17. The method of claim 15, wherein said expression vector further comprises a second reporter gene encoding a second reporter polypeptide, said second reporter gene operably linked to said nucleotide sequence encoding said fusion protein.

18. The method of claim 15, wherein the population of cells is a mammalian cell population.

19. The method of claim 18, wherein the mammalian cell population is a human cell population.

20. The method of claim 15, wherein the first reporter polypeptide is a fluorescent polypeptide.

21. The method of claim 17, wherein the first or second reporter polypeptide is a fluorescent polypeptide.

22. The method of claim 17, wherein the first reporter polypeptide is a first fluorescent polypeptide and the second reporter polypeptide is a second fluorescent polypeptide, wherein each of said first and second fluorescent polypeptides is detectable as a distinct signal when co-expressed in a cell.

23. The method of claim 20, wherein the fluorescent polypeptide is a green fluorescent protein (GFP), an enhanced GFP (EGFP), a destabilized enhanced GFP (d1EGFP), a blue fluorescent protein (BFP), a yellow fluorescent protein (YFP), or a red fluoresent protein (RFP including DsRed2).

24. The method of claim 22, wherein either of the fluorescent polypeptides is a green fluorescent protein (GFP), an enhanced GFP (EGFP), a destabilized enhanced GFP (d1EGFP), or a blue fluorescent protein (BFP).

25. The method of claim 15, wherein the polypeptide sequence is encoded by a nucleotide sequence from a nucleic acid library.

26. The method of claim 17, further comprising selecting for cells expressing the second reporter gene of step (b) prior to performing step (c).

27. The method of claim 15, wherein said assessing further comprises selecting for cells of said first sub-population treated with an extracellular stimulus of step (d) expressing the first reporter gene.

28. The method of claim 27, further comprising isolating DNA from said cells of said first sub-population treated with an extracellular stimulus of step (d) expressing the first reporter gene.

* * * * *